US012653607B2

(12) United States Patent
     Curran et al.

(10) Patent No.: US 12,653,607 B2
(45) Date of Patent: Jun. 16, 2026

(54) INTRAVASCULAR CATHETER TIP ELECTRODE ASSEMBLIES

(71) Applicant: St. Jude Medical, Cardiology Division, Inc., St. Paul, MN (US)

(72) Inventors: Timothy G. Curran, St. Paul, MN (US); Gregory K. Olson, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 772 days.

(21) Appl. No.: 17/256,551

(22) PCT Filed: Sep. 23, 2019

(86) PCT No.: PCT/IB2019/058052
     § 371 (c)(1),
     (2) Date: Dec. 28, 2020

(87) PCT Pub. No.: WO2020/065500
     PCT Pub. Date: Apr. 2, 2020

(65) Prior Publication Data
     US 2021/0220047 A1     Jul. 22, 2021

Related U.S. Application Data

(60) Provisional application No. 62/738,473, filed on Sep. 28, 2018.

(51) Int. Cl.
     *A61B 18/14* (2006.01)
     *A61B 18/00* (2006.01)

(52) U.S. Cl.
     CPC ..................... *A61B 18/1492* (2013.01); *A61B 2018/00351* (2013.01); *A61B 2018/00577* (2013.01);
     (Continued)

(58) Field of Classification Search
     CPC ........... A61B 2018/00351; A61B 2018/00577; A61B 2018/00839; A61B 2018/00875;
     (Continued)

(56) References Cited

U.S. PATENT DOCUMENTS

| 5,224,939 A | 7/1993 | Holman et al. |
| 5,239,999 A | 8/1993 | Imran |

(Continued)

FOREIGN PATENT DOCUMENTS

| CN | 101927053 B | 1/2015 |
| CN | 103157168 B | 4/2015 |

(Continued)

OTHER PUBLICATIONS

Magtibay et al., JAHA 2017 (J Am Heart Assoc. 2017;6:e006447. DOI: 10.1161/JAHA.117.006447). pp. 6-7, and section titled "Omnipoles Provide the Largest Possible Bipolar Voltages".

(Continued)

*Primary Examiner* — Michael F Peffley
*Assistant Examiner* — Bo Ouyang
(74) *Attorney, Agent, or Firm* — Kilpatrick Townsend & Stockton LLP

(57) ABSTRACT

Aspects of the present disclosure are directed to intravascular electrophysiology catheters which utilize electrodes on flexible electronic circuit(s) to facilitate reduced assembly complexity and cost. In one example embodiment, a distal tip assembly of an electrophysiology catheter is disclosed. The distal tip assembly including a catheter shaft, flexible circuitry, and a distal tip coupled to a distal end of the catheter shaft. The catheter shaft includes an outer surface with a trench extending into the outer surface, and the flexible circuitry is inserted into the trench and coupled to the catheter shaft. The flexible circuitry includes one or more (Continued)

electrodes configured and arranged to sense electrophysiological characteristics of tissue.

20 Claims, 9 Drawing Sheets

(52) U.S. Cl.
CPC .............. *A61B 2018/00839* (2013.01); *A61B 2018/00875* (2013.01); *A61B 2018/1435* (2013.01); *A61B 2018/1467* (2013.01)

(58) Field of Classification Search
CPC .... A61B 2018/1435; A61B 2018/1467; A61B 18/1492
See application file for complete search history.

(56) References Cited

U.S. PATENT DOCUMENTS

| | | | |
|---|---|---|---|
| 5,380,301 A | 1/1995 | Prichard et al. |
| 5,400,783 A | 3/1995 | Pomeranz et al. |
| 5,456,254 A | 10/1995 | Pietroski et al. |
| 5,626,136 A | 5/1997 | Webster, Jr. |
| 5,715,817 A | 2/1998 | Stevens-Wright et al. |
| 5,715,832 A | 2/1998 | Koblish et al. |
| 5,827,278 A | 10/1998 | Webster, Jr. |
| 5,876,373 A | 3/1999 | Giba et al. |
| 6,074,379 A | 6/2000 | Prichard |
| 6,233,476 B1 | 5/2001 | Strommer et al. |
| 6,273,404 B1 | 8/2001 | Holman et al. |
| 6,491,681 B1 | 12/2002 | Kunis et al. |
| 6,498,944 B1 | 12/2002 | Ben-Haim et al. |
| 6,554,794 B1 | 4/2003 | Mueller et al. |
| 6,690,963 B2 | 2/2004 | Ben-Haim et al. |
| 6,788,967 B2 | 9/2004 | Ben-Haim et al. |
| 7,004,937 B2 | 2/2006 | Lentz et al. |
| 7,197,354 B2 | 3/2007 | Sobe |
| 7,214,220 B2 | 5/2007 | McGlinch et al. |
| 7,217,256 B2 | 5/2007 | Di Palma |
| 7,263,397 B2 | 8/2007 | Hauck et al. |
| 7,386,339 B2 | 6/2008 | Strommer |
| 7,536,218 B2 | 5/2009 | Govari et al. |
| 7,608,063 B2 | 10/2009 | Le et al. |
| 7,625,365 B2 | 12/2009 | McGlinch et al. |
| 7,666,204 B2 | 2/2010 | Thornton et al. |
| 7,959,601 B2 | 6/2011 | McDaniel et al. |
| 7,985,215 B2 | 7/2011 | Guo et al. |
| 8,103,327 B2 | 1/2012 | Harlev et al. |
| 8,137,321 B2 | 3/2012 | Argentine |
| 8,187,267 B2 | 5/2012 | Pappone et al. |
| 8,206,404 B2 | 6/2012 | de la Rama et al. |
| 8,221,390 B2 | 7/2012 | Pal et al. |
| 8,273,016 B2 | 9/2012 | O'Sullivan |
| 8,376,990 B2 | 2/2013 | Ponzi et al. |
| 8,447,377 B2 | 5/2013 | Harlev et al. |
| 8,608,703 B2 | 12/2013 | Riles et al. |
| 8,649,880 B1 | 2/2014 | Parker, Jr. |
| 8,700,120 B2 | 4/2014 | Koblish |
| 8,706,193 B2 | 4/2014 | Govari et al. |
| 8,755,861 B2 | 6/2014 | Harlev et al. |
| 8,771,267 B2 | 7/2014 | Kunis et al. |
| 8,777,929 B2 | 7/2014 | Schneider et al. |
| 8,792,962 B2 | 7/2014 | Esguerra et al. |
| 8,814,824 B2 | 8/2014 | Kauphusman et al. |
| 8,814,825 B2 | 8/2014 | Tegg et al. |
| 8,882,705 B2 | 11/2014 | McDaniel et al. |
| 8,894,610 B2 | 11/2014 | Macnamara et al. |
| 8,979,841 B2 | 3/2015 | Kunis et al. |
| 8,996,091 B2 | 3/2015 | de la Rama et al. |
| 9,017,308 B2 | 4/2015 | Klisch et al. |
| 9,033,917 B2 | 5/2015 | Magana et al. |
| 9,050,010 B2 | 6/2015 | Bui et al. |
| 9,101,733 B2 | 8/2015 | McDaniel |
| 9,204,929 B2 | 12/2015 | Solis |
| 9,216,056 B2 | 12/2015 | Datta et al. |
| 9,247,990 B2 | 2/2016 | Kauphusman et al. |
| 9,326,815 B2 | 5/2016 | Watson |
| 9,339,631 B2 | 5/2016 | Graham et al. |
| 9,433,751 B2 | 9/2016 | Ponzi et al. |
| 9,433,752 B2 | 9/2016 | Jimenez et al. |
| 9,468,495 B2 | 10/2016 | Kunis et al. |
| 9,474,486 B2 | 10/2016 | Eliason et al. |
| 9,486,280 B2 | 11/2016 | Koblish et al. |
| 9,486,282 B2 | 11/2016 | Solis |
| 9,522,035 B2 | 12/2016 | Highsmith |
| 9,539,413 B2 | 1/2017 | Ogle |
| 9,629,675 B2 | 4/2017 | Kleshinski et al. |
| 9,649,158 B2 | 5/2017 | Datta et al. |
| 9,687,166 B2 | 6/2017 | Subramaniam et al. |
| 9,693,733 B2 | 7/2017 | Altmann et al. |
| 9,694,159 B2 | 7/2017 | Schneider et al. |
| 9,694,161 B2 | 7/2017 | Selkee |
| 9,788,895 B2 | 10/2017 | Solis |
| 9,820,664 B2 | 11/2017 | Hoitink et al. |
| 9,844,645 B2 | 12/2017 | Pai et al. |
| 9,848,795 B2 | 12/2017 | Marecki et al. |
| 9,919,132 B2 | 3/2018 | Tegg et al. |
| 9,949,656 B2 | 4/2018 | Wu et al. |
| 9,986,949 B2 | 6/2018 | Govari et al. |
| 10,004,877 B2 | 6/2018 | Tegg |
| 10,034,637 B2 | 7/2018 | Harlev et al. |
| 10,052,457 B2 | 8/2018 | Nguyen et al. |
| 10,065,019 B2 | 9/2018 | Hamuro et al. |
| 10,099,036 B2 | 10/2018 | Heideman et al. |
| 10,118,022 B2 | 11/2018 | Helgeson et al. |
| 10,130,423 B1 | 11/2018 | Viswanathan et al. |
| 10,136,829 B2 | 11/2018 | Deno et al. |
| 10,143,394 B2 | 12/2018 | Solis |
| 10,172,673 B2 | 1/2019 | Viswanathan et al. |
| 10,322,261 B2 | 6/2019 | Pai et al. |
| 10,362,952 B2 | 7/2019 | Basu et al. |
| 10,362,954 B2 | 7/2019 | de la Rama et al. |
| 10,376,170 B2 | 8/2019 | Quinn et al. |
| 10,384,036 B2 | 8/2019 | Romoscanu |
| 10,398,500 B2 | 9/2019 | Huszar et al. |
| 10,470,682 B2 | 11/2019 | Deno et al. |
| 10,478,247 B2 | 11/2019 | Litscher et al. |
| 10,478,325 B2 | 11/2019 | Syed |
| 10,492,729 B2 | 12/2019 | de la Rama et al. |
| 10,506,938 B2 | 12/2019 | Wu et al. |
| 10,537,259 B2 | 1/2020 | Wu et al. |
| 10,542,899 B2 | 1/2020 | Wu et al. |
| 10,556,089 B2 | 2/2020 | Scott et al. |
| 10,556,091 B2 | 2/2020 | Truhler et al. |
| 10,575,742 B2 | 3/2020 | Wu et al. |
| 10,575,745 B2 | 3/2020 | Solis |
| 10,595,738 B2 | 3/2020 | Sterrett et al. |
| 10,595,740 B2 | 3/2020 | Hoitink et al. |
| 10,602,948 B2 | 3/2020 | Wu et al. |
| 10,646,692 B2 | 5/2020 | Tegg et al. |
| 10,653,423 B2 | 5/2020 | Starnes |
| 10,702,677 B2 | 7/2020 | Okamura et al. |
| 10,737,060 B2 | 8/2020 | Gupta et al. |
| 10,813,590 B2 | 10/2020 | Ruppersberg |
| 10,835,712 B2 | 11/2020 | Wada |
| 10,842,990 B2 | 11/2020 | de la Rama et al. |
| 10,857,349 B2 | 12/2020 | de la Rama et al. |
| 10,869,992 B2 | 12/2020 | Pai et al. |
| 10,898,685 B2 | 1/2021 | Tegg |
| 10,912,925 B2 | 2/2021 | Houck |
| 10,932,685 B2 | 3/2021 | Wu |
| 10,945,626 B2 | 3/2021 | Fuentes-Ortega et al. |
| 10,946,167 B2 | 3/2021 | Mintz et al. |
| 10,953,196 B2 | 3/2021 | Raab et al. |
| 10,959,636 B2 | 3/2021 | Dahlen et al. |
| 10,966,623 B2 | 4/2021 | Wu et al. |
| 10,966,753 B2 | 4/2021 | Coyle et al. |
| 10,967,150 B2 | 4/2021 | Helgeson et al. |
| 10,987,045 B2 | 4/2021 | Basu et al. |
| 11,033,715 B2 | 6/2021 | Beeckler et al. |
| 11,039,772 B2 | 6/2021 | Wu et al. |
| 11,039,773 B2 | 6/2021 | Sterrett et al. |
| 11,077,298 B2 | 8/2021 | Waldhauser et al. |

(56)  References Cited

U.S. PATENT DOCUMENTS

| | | |
|---|---|---|
| 11,083,400 B2 | 8/2021 | Hoitink et al. |
| 11,116,436 B2 | 9/2021 | Wu et al. |
| 11,116,476 B2 | 9/2021 | Buesseler et al. |
| 11,123,051 B2 | 9/2021 | Van Der Linde et al. |
| 11,141,568 B2 | 10/2021 | Hsueh et al. |
| 11,160,482 B2 | 11/2021 | Solis |
| 11,172,858 B2 | 11/2021 | Olson et al. |
| D940,310 S | 1/2022 | de la Rama et al. |
| 11,272,886 B2 | 3/2022 | Harlev et al. |
| D951,438 S | 5/2022 | de la Rama et al. |
| D952,140 S | 5/2022 | de la Rama et al. |
| D952,843 S | 5/2022 | de la Rama et al. |
| 11,382,690 B2 | 7/2022 | Smith et al. |
| 11,382,743 B2 | 7/2022 | Marchand et al. |
| 11,383,078 B2 | 7/2022 | de la Rama et al. |
| 11,419,673 B2 | 8/2022 | Kauphusman et al. |
| 11,426,111 B2 | 8/2022 | Olson |
| 11,433,220 B2 | 9/2022 | Oliverius et al. |
| 11,439,460 B2 | 9/2022 | Sliwa et al. |
| 11,446,471 B2 | 9/2022 | Grunewald |
| D966,506 S | 10/2022 | de la Rama et al. |
| D966,507 S | 10/2022 | de la Rama et al. |
| 11,478,299 B2 | 10/2022 | Webster et al. |
| 11,484,690 B2 | 11/2022 | Tegg et al. |
| 11,491,311 B2 | 11/2022 | Selkee |
| 11,504,205 B2 | 11/2022 | Brucker et al. |
| 11,511,078 B2 | 11/2022 | Gonzalez |
| 11,517,715 B2 | 12/2022 | Govari |
| 11,523,748 B2 | 12/2022 | Esguerra Wilczynski et al. |
| 11,540,876 B2 | 1/2023 | Oliverius et al. |
| 11,547,437 B2 | 1/2023 | Zarembinski |
| 11,559,663 B2 | 1/2023 | Hannon et al. |
| 11,583,334 B2 | 2/2023 | Caples et al. |
| 11,602,630 B2 | 3/2023 | Vetter et al. |
| 11,617,616 B2 | 4/2023 | Clark et al. |
| 11,617,859 B2 | 4/2023 | Hsueh et al. |
| 11,617,861 B2 | 4/2023 | Pai et al. |
| 11,622,806 B2 | 4/2023 | Romoscanu |
| 11,628,009 B2 | 4/2023 | Aujla |
| 11,660,119 B2 | 5/2023 | Hassett |
| 11,672,947 B2 | 6/2023 | Tegg et al. |
| 11,723,574 B2 | 8/2023 | Wu et al. |
| 11,786,301 B2 | 10/2023 | Olson |
| 11,806,152 B2 | 11/2023 | Zeidan et al. |
| 11,813,410 B2 | 11/2023 | Olson et al. |
| 11,857,250 B2 | 1/2024 | Corvi et al. |
| 11,938,316 B2 | 3/2024 | Feler et al. |
| 11,950,897 B2 | 4/2024 | Esguerra Wilczynski et al. |
| 11,957,847 B2 | 4/2024 | Houck |
| 11,992,321 B2 | 5/2024 | Solis |
| 12,004,805 B2 | 6/2024 | Schuler et al. |
| 12,011,216 B2 | 6/2024 | Zirkle et al. |
| 12,036,027 B2 | 7/2024 | Olson et al. |
| 12,036,371 B2 | 7/2024 | Hsueh et al. |
| 12,064,168 B2 | 8/2024 | Harlev et al. |
| 12,076,079 B2 | 9/2024 | Oliverius et al. |
| 12,089,940 B2 | 9/2024 | Hoitink et al. |
| 12,097,034 B2 | 9/2024 | Wu et al. |
| 12,109,031 B2 | 10/2024 | Deno et al. |
| 12,114,922 B2 | 10/2024 | Harlev et al. |
| 12,121,357 B2 | 10/2024 | de la Rama et al. |
| 12,121,438 B2 | 10/2024 | Dehdashtian et al. |
| 12,144,629 B2 | 11/2024 | Wu et al. |
| 12,185,961 B2 | 1/2025 | Nguyen et al. |
| 12,193,823 B2 | 1/2025 | Wu et al. |
| 12,194,251 B2 | 1/2025 | Tavallaei et al. |
| 12,214,206 B2 | 2/2025 | Ward et al. |
| 12,232,908 B2 | 2/2025 | Stigall et al. |
| 12,246,143 B2 | 3/2025 | Leeflang et al. |
| 12,256,913 B2 | 3/2025 | Nunan |
| 12,256,984 B2 | 3/2025 | Ku et al. |
| 12,263,338 B2 | 4/2025 | de la Rama et al. |
| 12,324,620 B2 | 6/2025 | de la Rama et al. |
| 12,337,124 B2 | 6/2025 | Campbell et al. |
| 2002/0165484 A1 | 11/2002 | Bowe et al. |

| | | | |
|---|---|---|---|
| 2005/0033136 A1* | 2/2005 | Govari | A61B 5/287 |
| | | | 606/41 |
| 2006/0167448 A1* | 7/2006 | Kozel | A61B 18/1492 |
| | | | 606/41 |
| 2009/0149848 A1* | 6/2009 | Werneth | A61B 18/18 |
| | | | 606/41 |
| 2010/0152731 A1 | 6/2010 | de la Rama et al. | |
| 2010/0174177 A1 | 7/2010 | Wu | |
| 2010/0286684 A1 | 11/2010 | Hata et al. | |
| 2011/0118582 A1 | 5/2011 | de la Rama et al. | |
| 2011/0288392 A1 | 11/2011 | De La Rama et al. | |
| 2012/0010490 A1 | 1/2012 | Kauphusman et al. | |
| 2012/0130218 A1* | 5/2012 | Kauphusman | A61B 5/6852 |
| | | | 600/585 |
| 2014/0100639 A1 | 4/2014 | Lee et al. | |
| 2015/0001191 A1 | 1/2015 | Lee et al. | |
| 2015/0126996 A1* | 5/2015 | Tegg | A61M 25/0012 |
| | | | 606/41 |
| 2015/0273184 A1* | 10/2015 | Scott | H01B 7/04 |
| | | | 29/842 |
| 2016/0213423 A1 | 7/2016 | Kauphusman et al. | |
| 2016/0278851 A1 | 9/2016 | Mannion et al. | |
| 2016/0331933 A1 | 11/2016 | Knutsen | |
| 2017/0042449 A1 | 2/2017 | Deno et al. | |
| 2017/0042615 A1* | 2/2017 | Salahieh | A61B 5/01 |
| 2017/0319269 A1 | 11/2017 | Oliverius et al. | |
| 2017/0367756 A1 | 12/2017 | Sliwa et al. | |
| 2018/0042667 A1 | 2/2018 | Pappone et al. | |
| 2018/0085064 A1 | 3/2018 | Auerbach et al. | |
| 2018/0116539 A1 | 5/2018 | Plson et al. | |
| 2018/0161093 A1 | 6/2018 | Basu et al. | |
| 2018/0229030 A1 | 8/2018 | Dubuclet et al. | |
| 2018/0369574 A1 | 12/2018 | Dubuclet et al. | |
| 2019/0009052 A1 | 1/2019 | Oliverius et al. | |
| 2019/0125378 A1 | 5/2019 | Shelton, IV et al. | |
| 2019/0192826 A1 | 6/2019 | Wada | |
| 2020/0000359 A1 | 1/2020 | de la Rama et al. | |
| 2020/0054391 A1 | 2/2020 | Litscher et al. | |
| 2020/0069365 A1 | 3/2020 | Harlev et al. | |
| 2020/0077908 A1 | 3/2020 | Hagfors et al. | |
| 2020/0121894 A1 | 4/2020 | Prabhu et al. | |
| 2020/0138378 A1 | 5/2020 | de la Rama et al. | |
| 2020/0214635 A1 | 7/2020 | Dahlen et al. | |
| 2020/0229866 A1 | 7/2020 | Harlev et al. | |
| 2020/0253496 A1 | 8/2020 | Deno et al. | |
| 2020/0405166 A1 | 12/2020 | Wu et al. | |
| 2021/0038860 A1 | 2/2021 | Mintz et al. | |
| 2021/0145342 A1 | 5/2021 | Wang | |
| 2021/0153932 A1 | 5/2021 | Voth et al. | |
| 2021/0187246 A1 | 6/2021 | Houck | |
| 2021/0204871 A1 | 7/2021 | Goedeke et al. | |
| 2021/0267693 A1 | 9/2021 | Deno et al. | |
| 2021/0268234 A1 | 9/2021 | Helgeson et al. | |
| 2021/0298656 A1 | 9/2021 | Wu et al. | |
| 2021/0361216 A1 | 11/2021 | Hoitink et al. | |
| 2021/0401345 A1 | 12/2021 | Wu et al. | |
| 2022/0023594 A1 | 1/2022 | Pai | |
| 2022/0054066 A1 | 2/2022 | Solis | |
| 2022/0061727 A1 | 3/2022 | Olson et al. | |
| 2022/0175445 A1 | 6/2022 | Sutermeister et al. | |
| 2022/0273913 A1 | 9/2022 | Worley et al. | |
| 2022/0354568 A1 | 11/2022 | Pappone et al. | |
| 2022/0370792 A1 | 11/2022 | de la Rama et al. | |
| 2022/0387012 A1 | 12/2022 | Nunan | |
| 2022/0401693 A1 | 12/2022 | Oliverius et al. | |
| 2023/0000415 A1 | 1/2023 | Olson | |
| 2023/0011509 A1 | 1/2023 | Sterrett et al. | |
| 2023/0078216 A1 | 3/2023 | Govari | |
| 2023/0084626 A1 | 3/2023 | Grunewald | |
| 2023/0114222 A1 | 4/2023 | Esguerra Wilczynski et al. | |
| 2023/0121397 A1 | 4/2023 | Oliverius et al. | |
| 2023/0172661 A1 | 6/2023 | Harlev et al. | |
| 2023/0190369 A1 | 6/2023 | Caples et al. | |
| 2023/0329618 A1 | 10/2023 | Wu et al. | |
| 2023/0329784 A1 | 10/2023 | Stewart et al. | |
| 2023/0404657 A1 | 12/2023 | Olson | |
| 2024/0033470 A1 | 2/2024 | Olson et al. | |
| 2024/0081905 A1 | 3/2024 | Corvi et al. | |
| 2024/0173070 A1 | 5/2024 | Selkee et al. | |

(56)                    References Cited

U.S. PATENT DOCUMENTS

| 2024/0198054 | A1 | 6/2024 | Schultz |
| 2024/0252815 | A1 | 8/2024 | de la Rama et al. |
| 2024/0277277 | A1 | 8/2024 | Hoitink et al. |
| 2024/0325691 | A1 | 10/2024 | Bogusky |
| 2024/0350063 | A1 | 10/2024 | Olson et al. |
| 2024/0366299 | A1 | 11/2024 | Dando et al. |
| 2024/0415438 | A1 | 12/2024 | Wu et al. |
| 2025/0009272 | A1 | 1/2025 | de la Rama et al. |
| 2025/0025231 | A1 | 1/2025 | Oliverius et al. |
| 2025/0032028 | A1 | 1/2025 | Deno et al. |
| 2025/0032181 | A1 | 1/2025 | Harlev et al. |
| 2025/0040853 | A1 | 2/2025 | Wu et al. |
| 2025/0049460 | A1 | 2/2025 | Worrell et al. |
| 2025/0072897 | A1 | 3/2025 | Reu et al. |
| 2025/0082438 | A1 | 3/2025 | Seeralan et al. |
| 2025/0082903 | A1 | 3/2025 | Hsueh et al. |
| 2025/0090070 | A1 | 3/2025 | Wu et al. |
| 2025/0090807 | A1 | 3/2025 | Padilla et al. |
| 2025/0152932 | A1 | 5/2025 | de la Rama et al. |
| 2025/0160942 | A1 | 5/2025 | Ku et al. |

FOREIGN PATENT DOCUMENTS

| CN | 106859765 | A | 6/2017 |
| CN | 106901831 | A | 6/2017 |
| CN | 206880930 | U | 1/2018 |
| CN | 104958824 | B | 12/2018 |
| CN | 104434083 | B | 4/2019 |
| CN | 104968261 | B | 5/2019 |
| CN | 105592778 | B | 7/2019 |
| CN | 105960200 | B | 8/2019 |
| CN | 105451680 | B | 10/2019 |
| CN | 110536646 | A | 12/2019 |
| CN | 110604860 | A | 12/2019 |
| CN | 105960201 | B | 3/2020 |
| CN | 111225627 | A | 6/2020 |
| CN | 111432739 | A | 7/2020 |
| CN | 111657866 | A | 9/2020 |
| CN | 106264715 | B | 11/2020 |
| CN | 106264716 | B | 11/2020 |
| CN | 112040861 | A | 12/2020 |
| CN | 106308790 | B | 6/2021 |
| CN | 107529958 | B | 7/2021 |
| CN | 109310469 | B | 7/2021 |
| CN | 109641121 | B | 9/2021 |
| CN | 109952123 | B | 9/2021 |
| CN | 110545874 | B | 9/2021 |
| CN | 110559544 | B | 9/2021 |
| CN | 113425304 | A | 9/2021 |
| CN | 105615994 | B | 10/2021 |
| CN | 109963610 | B | 11/2021 |
| CN | 108289709 | B | 3/2022 |
| CN | 111246907 | B | 7/2022 |
| CN | 107773300 | B | 8/2022 |
| CN | 108567424 | B | 8/2022 |
| CN | 106859638 | B | 10/2022 |
| CN | 108283520 | B | 10/2022 |
| CN | 110547865 | B | 10/2022 |
| CN | 107343816 | B | 11/2022 |
| CN | 115281680 | A | 11/2022 |
| CN | 115444549 | A | 12/2022 |
| CN | 107343784 | B | 2/2023 |
| CN | 110520067 | B | 5/2023 |
| CN | 116158839 | A | 5/2023 |
| CN | 106419897 | B | 6/2023 |
| CN | 111065350 | B | 6/2023 |
| CN | 109259854 | B | 10/2023 |
| CN | 111657866 | B | 10/2023 |
| CN | 111836579 | B | 3/2024 |
| CN | 112704546 | B | 3/2024 |
| CN | 117942483 | A | 4/2024 |
| CN | 117958829 | A | 5/2024 |
| CN | 118384409 | A | 7/2024 |
| CN | 111683581 | B | 9/2024 |
| CN | 112040861 | B | 9/2024 |
| CN | 111683614 | B | 10/2024 |
| CN | 111918606 | B | 1/2025 |
| CN | 119385661 | A | 2/2025 |
| CN | 112040860 | B | 5/2025 |
| CN | 112135576 | B | 6/2025 |
| EP | 0889744 | B1 | 1/2004 |
| EP | 1254641 | B1 | 11/2008 |
| EP | 1690564 | B1 | 4/2009 |
| EP | 1723981 | B1 | 8/2010 |
| EP | 2135634 | B1 | 10/2011 |
| EP | 2018203 | B1 | 6/2012 |
| EP | 1814450 | B1 | 1/2013 |
| EP | 2269532 | B1 | 3/2013 |
| EP | 2604306 | B1 | 1/2014 |
| EP | 2752153 | A1 | 7/2014 |
| EP | 2915555 | A1 | 9/2015 |
| EP | 1968679 | B1 | 9/2016 |
| EP | 2241279 | B1 | 9/2016 |
| EP | 3115076 | A4 | 10/2017 |
| EP | 3117863 | A4 | 10/2017 |
| EP | 3030182 | B1 | 1/2018 |
| EP | 3111871 | B1 | 3/2018 |
| EP | 3111872 | B1 | 4/2018 |
| EP | 3057488 | B1 | 5/2018 |
| EP | 2848226 | B1 | 7/2018 |
| EP | 3363397 | A1 | 8/2018 |
| EP | 3391928 | A1 | 10/2018 |
| EP | 3122276 | B1 | 11/2018 |
| EP | 3398549 | A1 | 11/2018 |
| EP | 1759668 | B1 | 12/2018 |
| EP | 3037122 | B1 | 12/2018 |
| EP | 2234537 | B1 | 1/2019 |
| EP | 2569040 | B1 | 2/2019 |
| EP | 3023052 | B1 | 3/2019 |
| EP | 3466363 | A1 | 4/2019 |
| EP | 2550989 | B1 | 6/2019 |
| EP | 3512589 | A1 | 7/2019 |
| EP | 3512590 | A1 | 7/2019 |
| EP | 3527125 | A1 | 8/2019 |
| EP | 3531903 | A1 | 9/2019 |
| EP | 3581229 | A1 | 12/2019 |
| EP | 3434218 | B1 | 2/2020 |
| EP | 2908723 | B1 | 3/2020 |
| EP | 3335658 | B1 | 4/2020 |
| EP | 3073907 | B1 | 6/2020 |
| EP | 3114987 | B1 | 8/2020 |
| EP | 3178516 | B1 | 9/2020 |
| EP | 3708104 | A1 | 9/2020 |
| EP | 3711662 | A1 | 9/2020 |
| EP | 3721796 | A1 | 10/2020 |
| EP | 3738508 | A1 | 11/2020 |
| EP | 3738509 | A1 | 11/2020 |
| EP | 3340916 | B1 | 12/2020 |
| EP | 3579908 | B1 | 12/2020 |
| EP | 3749195 | A1 | 12/2020 |
| EP | 3750475 | A1 | 12/2020 |
| EP | 3768185 | A1 | 1/2021 |
| EP | 2155301 | B1 | 4/2021 |
| EP | 3432820 | B1 | 4/2021 |
| EP | 3476331 | B1 | 5/2021 |
| EP | 3579758 | B1 | 5/2021 |
| EP | 2809254 | B1 | 6/2021 |
| EP | 3508245 | B1 | 7/2021 |
| EP | 3858277 | A1 | 8/2021 |
| EP | 3892221 | A1 | 10/2021 |
| EP | 3932343 | A4 | 1/2022 |
| EP | 3791820 | B9 | 4/2022 |
| EP | 4000506 | A1 | 5/2022 |
| EP | 3153124 | B1 | 7/2022 |
| EP | 4039215 | A1 | 8/2022 |
| EP | 3609414 | B1 | 11/2022 |
| EP | 4101372 | A1 | 12/2022 |
| EP | 2844193 | B1 | 1/2023 |
| EP | 3100696 | B1 | 1/2023 |
| EP | 3166524 | B1 | 1/2023 |
| EP | 4115936 | A1 | 1/2023 |
| EP | 4134032 | A1 | 2/2023 |
| EP | 3115076 | B1 | 3/2023 |
| EP | 3658054 | B1 | 3/2023 |

(56) References Cited

FOREIGN PATENT DOCUMENTS

| | | | |
|---|---|---|---|
| EP | 4179991 | A1 | 5/2023 |
| EP | 2803329 | B1 | 6/2023 |
| EP | 3015064 | B1 | 6/2023 |
| EP | 3141183 | B1 | 6/2023 |
| EP | 3768185 | B1 | 6/2023 |
| EP | 4190232 | A1 | 6/2023 |
| EP | 2816966 | B1 | 10/2023 |
| EP | 3113671 | B1 | 10/2023 |
| EP | 3681427 | B1 | 10/2023 |
| EP | 3738509 | B1 | 10/2023 |
| EP | 3749195 | B1 | 10/2023 |
| EP | 3209234 | B1 | 11/2023 |
| EP | 3527125 | B1 | 11/2023 |
| EP | 3721796 | B1 | 11/2023 |
| EP | 3731747 | B1 | 11/2023 |
| EP | 4233699 | A3 | 11/2023 |
| EP | 4272631 | A2 | 11/2023 |
| EP | 3192442 | B1 | 1/2024 |
| EP | 3892221 | B1 | 1/2024 |
| EP | 4298995 | A2 | 1/2024 |
| EP | 3738508 | B1 | 2/2024 |
| EP | 3124069 | B1 | 4/2024 |
| EP | 4360572 | A1 | 5/2024 |
| EP | 4364765 | A2 | 5/2024 |
| EP | 3498156 | B1 | 6/2024 |
| EP | 4344722 | A3 | 6/2024 |
| EP | 3573559 | B1 | 7/2024 |
| EP | 4272631 | A3 | 7/2024 |
| EP | 3603493 | B1 | 8/2024 |
| EP | 4205685 | B1 | 8/2024 |
| EP | 4417112 | A2 | 8/2024 |
| EP | 3629964 | B1 | 9/2024 |
| EP | 3184035 | B1 | 10/2024 |
| EP | 4417112 | A3 | 11/2024 |
| EP | 4101372 | B1 | 12/2024 |
| EP | 4437989 | A3 | 12/2024 |
| EP | 3737453 | B1 | 1/2025 |
| EP | 2915555 | B1 | 2/2025 |
| JP | 4545384 | B2 | 7/2010 |
| JP | 4887810 | B2 | 2/2012 |
| JP | 4940332 | B2 | 3/2012 |
| JP | 2012055602 | A | 3/2012 |
| JP | 2012200509 | A | 10/2012 |
| JP | 5154031 | B2 | 2/2013 |
| JP | 5193190 | B2 | 5/2013 |
| JP | 5372314 | B2 | 12/2013 |
| JP | 2014014713 | A | 1/2014 |
| JP | 5550150 | B2 | 5/2014 |
| JP | 5762697 | B2 | 6/2015 |
| JP | 5856712 | B2 | 2/2016 |
| JP | 5908270 | B2 | 4/2016 |
| JP | 5944331 | B2 | 7/2016 |
| JP | 6050522 | B2 | 12/2016 |
| JP | 6059737 | B2 | 12/2016 |
| JP | 2017051211 | A | 3/2017 |
| JP | 2017104552 | A | 6/2017 |
| JP | 6246742 | B2 | 12/2017 |
| JP | 6342524 | B2 | 6/2018 |
| JP | 6434495 | B2 | 12/2018 |
| JP | 6445509 | B2 | 12/2018 |
| JP | 6445742 | B1 | 12/2018 |
| JP | 6466114 | B2 | 2/2019 |
| JP | 6479005 | B2 | 2/2019 |
| JP | 6515084 | B2 | 5/2019 |
| JP | 6528010 | B1 | 6/2019 |
| JP | 6655655 | B2 | 2/2020 |
| JP | 6746734 | B2 | 8/2020 |
| JP | 6776021 | B2 | 10/2020 |
| JP | 6776025 | B2 | 10/2020 |
| JP | 6786275 | B2 | 11/2020 |
| JP | 6821812 | B2 | 1/2021 |
| JP | 2021007772 | A | 1/2021 |
| JP | 2021501011 | A | 1/2021 |
| JP | 6843502 | B2 | 3/2021 |
| JP | 6894004 | B2 | 6/2021 |
| JP | 6920312 | B2 | 8/2021 |
| JP | 6926306 | B2 | 8/2021 |
| JP | 6932484 | B2 | 8/2021 |
| JP | 6936872 | B2 | 9/2021 |
| JP | 2021523755 | A | 9/2021 |
| JP | 6980386 | B2 | 12/2021 |
| JP | 2022020838 | A | 2/2022 |
| JP | 7101228 | B2 | 7/2022 |
| JP | 7102558 | B2 | 7/2022 |
| JP | 7106301 | B2 | 7/2022 |
| JP | 2023002720 | A | 1/2023 |
| JP | 7220242 | B2 | 2/2023 |
| JP | 7230168 | B2 | 2/2023 |
| JP | 7242665 | B2 | 3/2023 |
| JP | 7242816 | B2 | 3/2023 |
| JP | 7246319 | B2 | 3/2023 |
| JP | 2023027202 | A | 3/2023 |
| JP | 2023033335 | A | 3/2023 |
| JP | 7256621 | B2 | 4/2023 |
| JP | 7262919 | B2 | 4/2023 |
| JP | 7275333 | B2 | 5/2023 |
| JP | 7282759 | B2 | 5/2023 |
| JP | 7292822 | B2 | 6/2023 |
| JP | 7391562 | B2 | 11/2023 |
| JP | 7394766 | B2 | 11/2023 |
| JP | 7400050 | B2 | 12/2023 |
| JP | 7423550 | B2 | 1/2024 |
| JP | 2024012693 | A | 1/2024 |
| JP | 7465944 | B2 | 4/2024 |
| JP | 2024059810 | A | 5/2024 |
| JP | 7499702 | B2 | 6/2024 |
| JP | 7514764 | B2 | 7/2024 |
| JP | 7517994 | B2 | 8/2024 |
| JP | 7530317 | B2 | 8/2024 |
| JP | 2024103761 | A | 8/2024 |
| JP | 2024125304 | A | 9/2024 |
| JP | 2024156696 | A | 11/2024 |
| JP | 2025013792 | A | 1/2025 |
| JP | 7628563 | B2 | 2/2025 |
| JP | 7639079 | B2 | 2/2025 |
| JP | 2025026734 | A | 2/2025 |
| JP | 2025026852 | A | 2/2025 |
| JP | 2025027101 | A | 2/2025 |
| JP | 7641330 | B2 | 3/2025 |
| JP | 7646980 | B2 | 4/2025 |
| WO | 199519318 | A1 | 4/1995 |
| WO | 9843530 | A1 | 10/1998 |
| WO | 0168178 | A1 | 9/2001 |
| WO | 2008091197 | A1 | 7/2008 |
| WO | 2011159861 | A2 | 12/2011 |
| WO | 2011159955 | A1 | 12/2011 |
| WO | 2014113612 | A1 | 7/2014 |
| WO | 2015130824 | A1 | 9/2015 |
| WO | 2016112196 | A1 | 7/2016 |
| WO | 2017098198 | A1 | 6/2017 |
| WO | 2018053148 | A1 | 3/2018 |
| WO | 2018053164 | A1 | 3/2018 |
| WO | 2018136741 | A1 | 7/2018 |
| WO | 2019074733 | A1 | 4/2019 |
| WO | 2019195439 | A1 | 10/2019 |

OTHER PUBLICATIONS

Haldar et al., Circulation AE 2017 (Circ Arrhythm Electrophysiol. 2017;10:e005018. DOI:10.1161/circep.117.005018) p. 6, "Omnipolar Voltage Amplitude Correlates to Largest Measurable Bipolar Vpp" and Fig. 4.

* cited by examiner

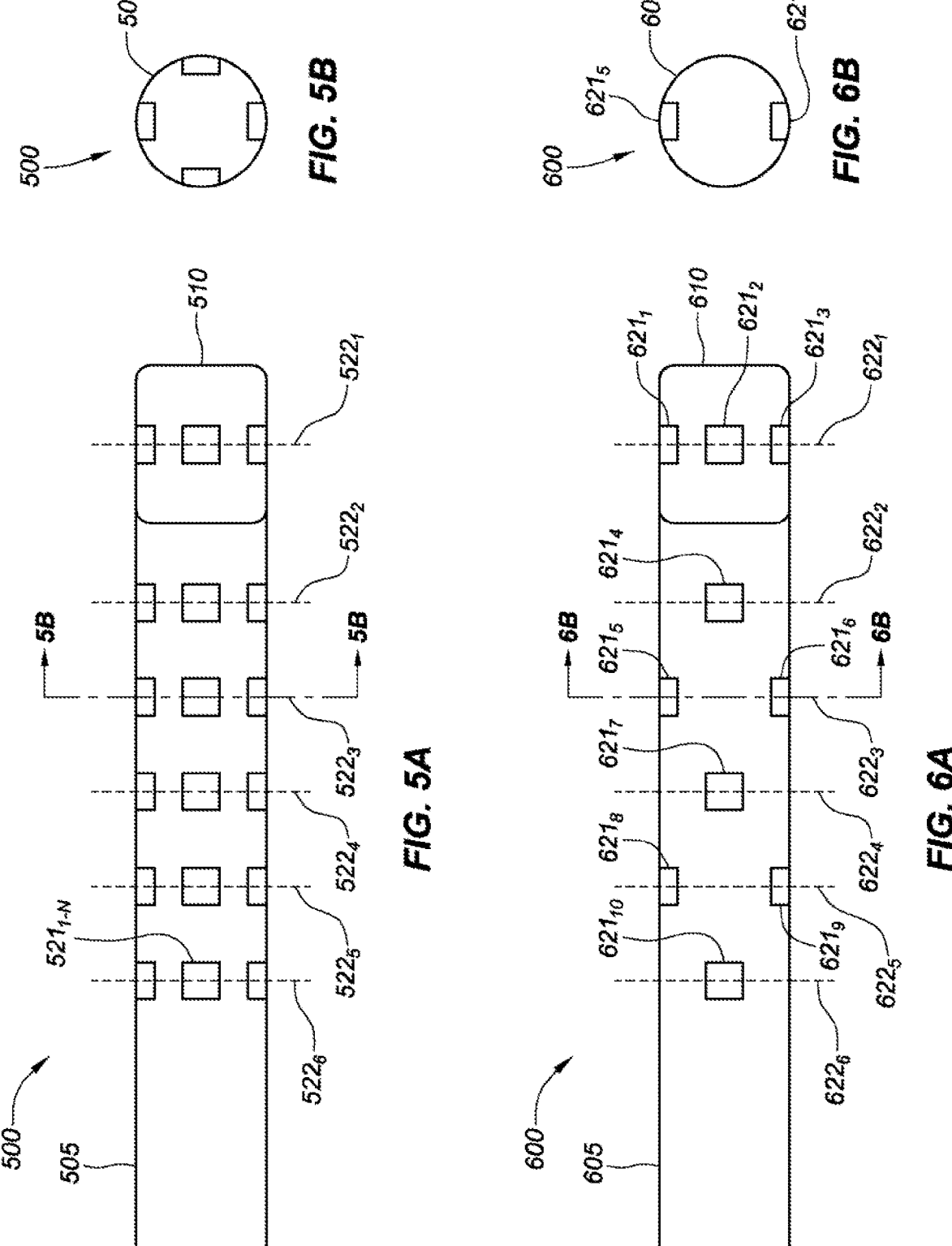

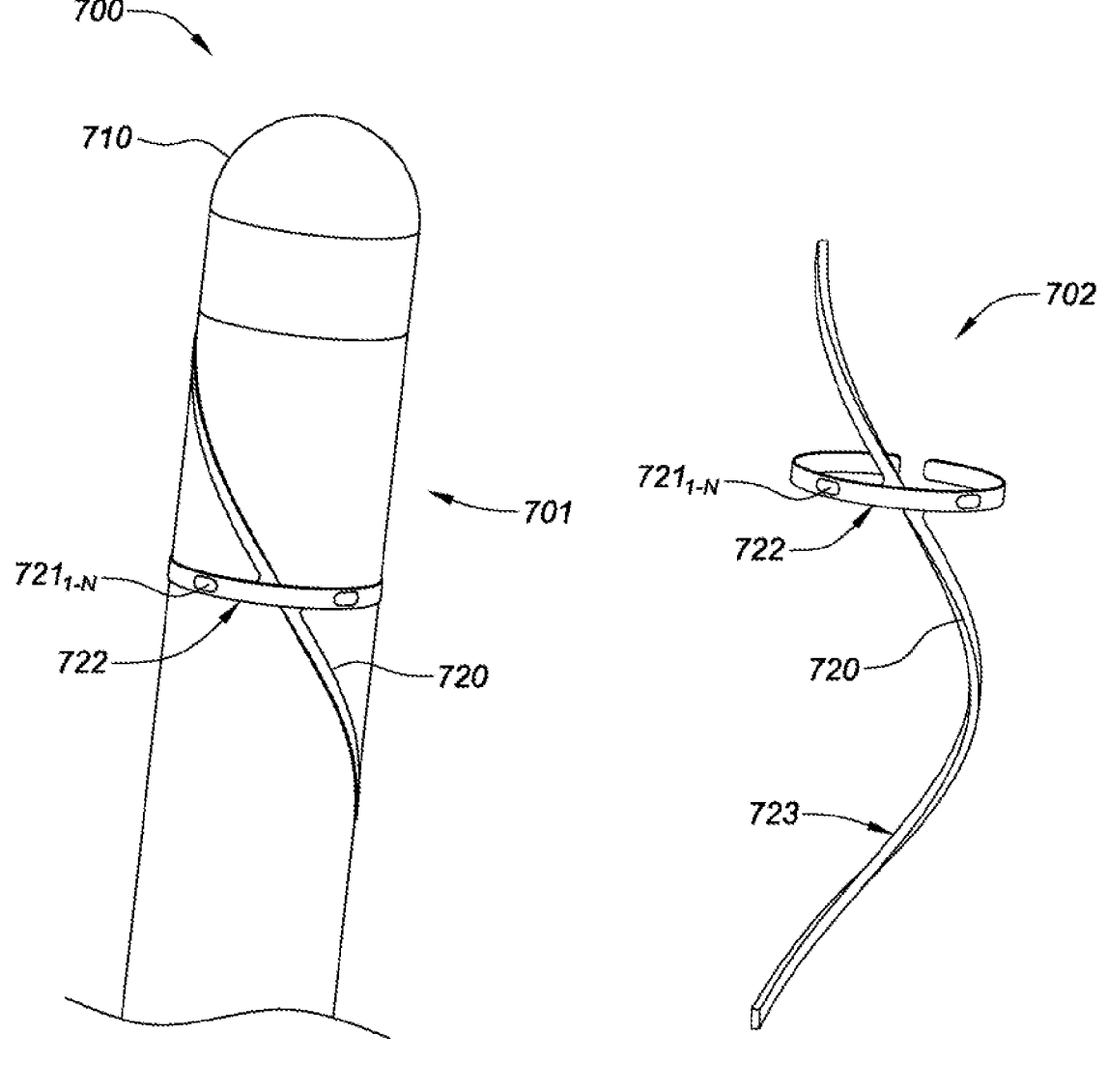
FIG. 7A          FIG. 7B

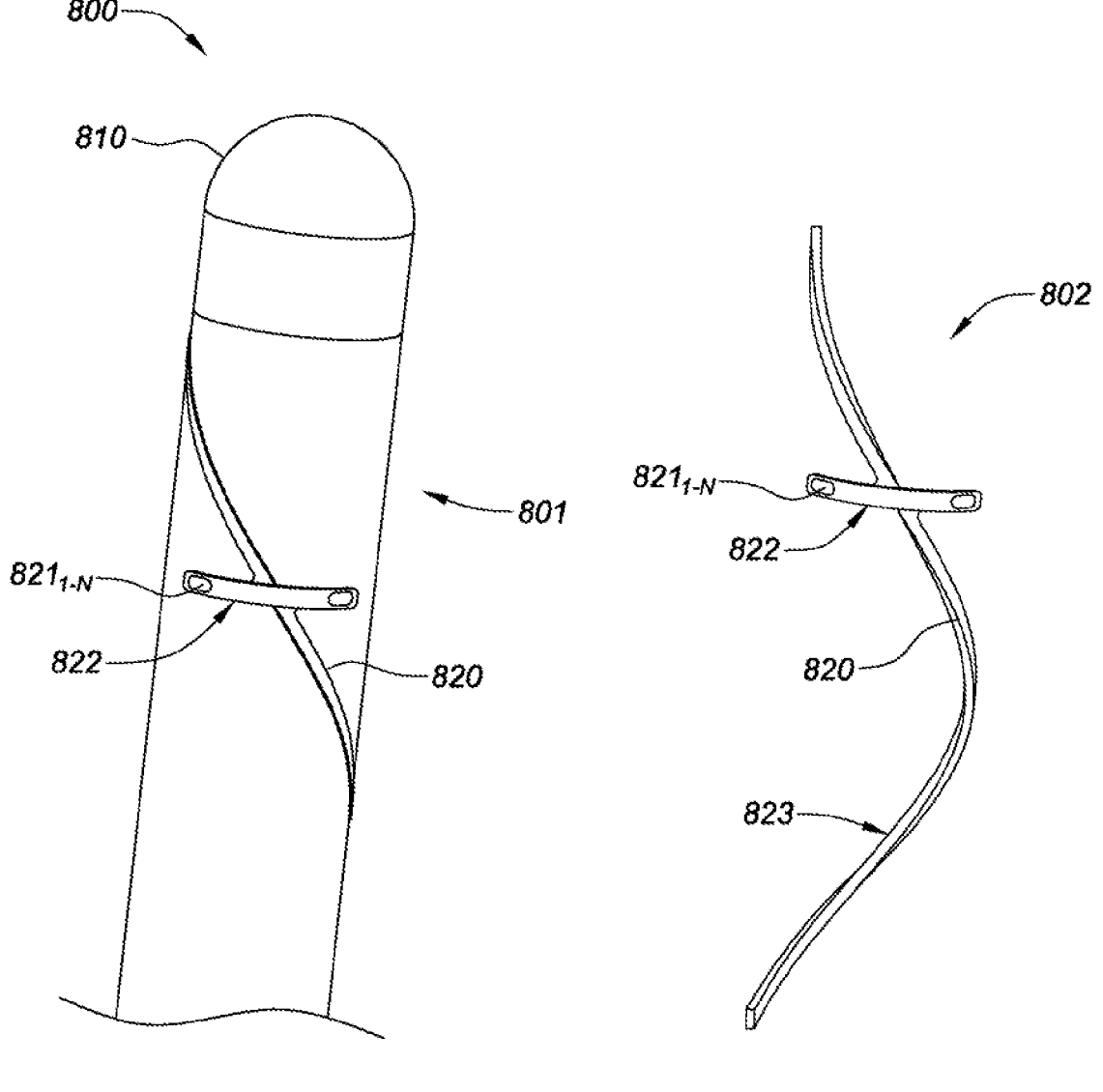
FIG. 8A                              FIG. 8B

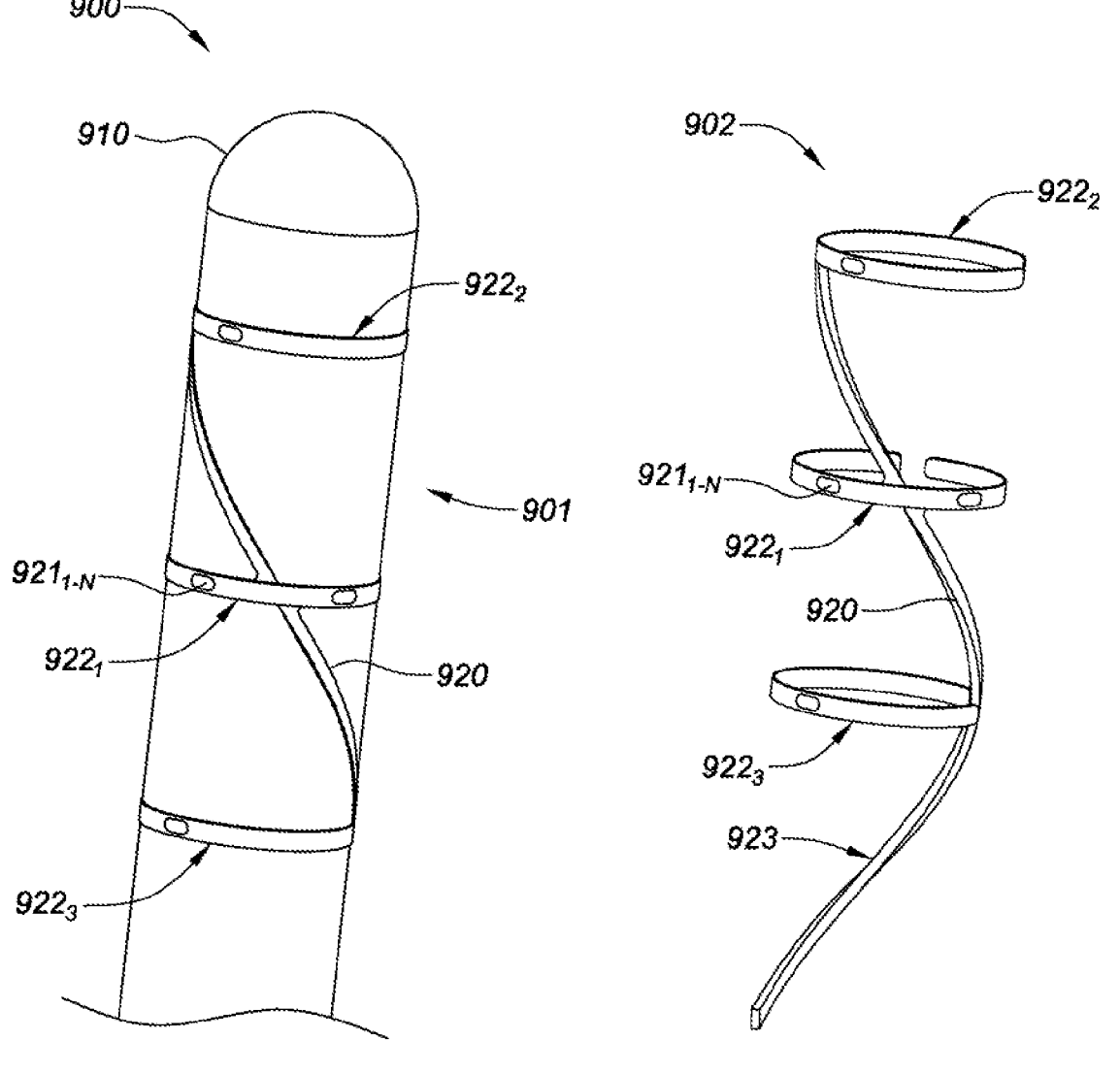
*FIG. 9A*          *FIG. 9B*

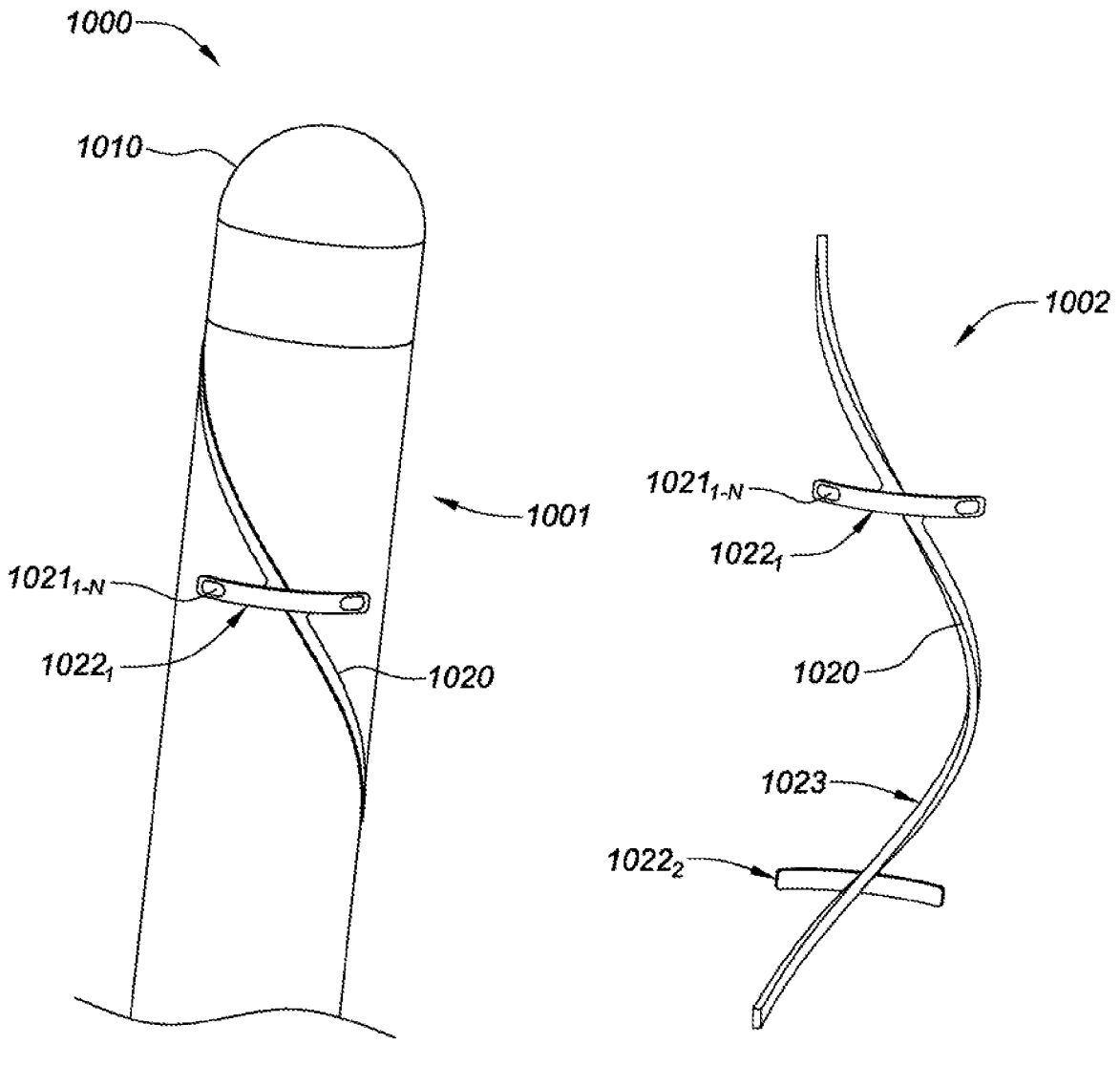
FIG. 10A            FIG. 10B

INTRAVASCULAR CATHETER TIP ELECTRODE ASSEMBLIES

CROSS-REFERENCE TO RELATED APPLICATIONS

This application is the national stage of International Application No. PCT/IB2019/058052, filed 23 Sep. 2019, which claims the benefit of U.S. provisional application No. 62/738,473, filed 28 Sep. 2018, which are hereby incorporated by reference as though fully set forth herein.

BACKGROUND OF THE INVENTION a. Field of the Invention

The present disclosure relates to the design and manufacture of intravascular catheters; more specifically, electrode assemblies for use in intravascular catheters.

b. Background Art

Electrophysiology catheters are used in a variety of diagnostic and/or therapeutic medical procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

Medical procedures for diagnosing and/or treating arrhythmias may utilize an electrophysiology catheter deployed through a patient's vasculature to a patient's heart (or a chamber or vein thereof). The electrophysiology catheter carries one or more electrodes that can be used for cardiac mapping or diagnosis, ablation and/or other therapy delivery modes, or both. Once at the intended site, treatment may include radio frequency (RF) ablation, cryoablation, laser ablation, chemical ablation, high-intensity focused ultrasound-based ablation, microwave ablation, etc. The electrophysiology catheter may impart ablative energy to cardiac tissue to create one or more lesions in the cardiac tissue and oftentimes a contiguous or linear, and transmural lesion. This lesion disrupts undesirable cardiac activation pathways and thereby limits, corrals, or prevents stray/errant conduction signals that can form the basis for arrhythmias. As readily apparent, such diagnosis and therapy delivery requires precise diagnostic mapping and treatment.

While prior art basket catheters, such as the TOPERA FIRMap™ (now owned by Abbott Medical Systems) diagnostic cardiac catheter, have implemented spot electrodes on flexible printed circuitry to facilitate electrophysiology mapping of target tissue, the difficulties of implementing flexible circuit technology on the distal tip of linear electrophysiology (EP) catheters have resulted in the continued use of ring electrodes thereon.

BRIEF SUMMARY OF THE INVENTION

The instant disclosure relates to intravascular catheter apparatus (and systems), and the manufacture thereof; more specifically, aspects of the present disclosure are directed to high-density mapping catheters and to map-ablate catheters for diagnosing and treating cardiac arrhythmias, for example. In particular, the instant disclosure relates to high density mapping/ablation catheters that include high-density mapping electrodes coupled to flexible circuitry which facilitate improved assembly efficacy and cost.

One embodiment of the present disclosure is directed to a distal tip assembly of an electrophysiology catheter. The distal tip assembly includes a catheter shaft, flexible circuitry, and a distal tip. The catheter shaft includes an outer surface with a trench extending into the outer surface. The flexible circuitry is inserted into the trench and coupled to the catheter shaft. The flexible circuitry includes one or more electrodes that sense electrophysiological characteristics of tissue. The distal tip is coupled to the distal end of the catheter shaft. In some embodiments, the electrodes are spot electrodes, and a top surface of the spot electrodes are flush with the outer surface of the catheter shaft. In various specific embodiments, the trench extends helically about the catheter shaft, the one or more spot electrodes are spaced along a length of the flexible circuitry, and thereby are circumferentially and longitudinally distributed about the catheter shaft.

Aspects of the present disclosure are directed to an electrophysiology catheter system. The system including a catheter and controller circuitry. The catheter includes a catheter shaft with a trench extending into an outer surface thereof, a distal tip coupled to the distal end of the catheter shaft, a catheter handle coupled to a proximal end of the catheter shaft, and flexible circuitry inserted into the trench and coupled to the catheter shaft. The flexible circuitry includes one or more electrodes that sense electrophysiological characteristics of tissue. The controller circuitry is communicatively coupled to the electrodes via the flexible circuitry. The controller circuitry receives signals from the electrodes indicative of the electrophysiological characteristics of tissue in contact with the electrodes. In more specific embodiments, the flexible circuitry includes a plurality of internal electrical traces extending along one or more substrate layers. The traces communicatively couple the electrodes to the controller circuitry. The electrodes are ring electrodes which surround at least a portion of the catheter shaft, and are electrically coupled with at least one of the plurality of electrical traces on the flexible circuitry. The catheter further includes a biocompatible outer covering extending over at least a portion of the flexible circuitry and the catheter shaft.

Yet further embodiments of the present disclosure are directed to a distal tip assembly of an electrophysiology catheter. The distal tip assembly includes a catheter shaft, flexible circuitry, and a distal tip coupled to a distal end of the catheter shaft. The flexible circuitry circumferentially extends about, and is coupled to, the catheter shaft. The flexible circuitry includes one or more spot electrodes that sense electrophysiological characteristics of tissue. In some embodiments, the flexible circuitry is coupled to the catheter shaft via a reflow process.

The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings, in which:

FIG. 5A is a side view of an electrophysiology catheter tip, consistent with various embodiments of the present disclosure;

FIG. 5B is a cross-sectional front view of the electrophysiology catheter tip of FIG. 5A, consistent with various embodiments of the present disclosure;

FIG. 6A is a side view of an electrophysiology catheter tip, consistent with various embodiments of the present disclosure;

FIG. 6B is a cross-sectional front view of the electrophysiology catheter tip of FIG. 6A, consistent with various embodiments of the present disclosure;

FIG. 7A is an isometric front view of an assembled electrophysiology catheter tip, consistent with various embodiments of the present disclosure;

FIG. 7B is an isometric front view of a partially-assembled electrophysiology catheter tip of FIG. 7A, consistent with various embodiments of the present disclosure;

FIG. 8A is an isometric front view of an assembled electrophysiology catheter tip, consistent with various embodiments of the present disclosure;

FIG. 8B is an isometric front view of a partially-assembled electrophysiology catheter tip of FIG. 8A, consistent with various embodiments of the present disclosure;

FIG. 9A is an isometric front view of an assembled electrophysiology catheter tip, consistent with various embodiments of the present disclosure;

FIG. 9B is an isometric front view of a partially-assembled electrophysiology catheter tip of FIG. 9A, consistent with various embodiments of the present disclosure;

FIG. 10A is an isometric front view of an assembled electrophysiology catheter tip, consistent with various embodiments of the present disclosure; and FIG. 10B is an isometric front view of a partially-assembled electrophysiology catheter tip of FIG. 10A, consistent with various embodiments of the present disclosure.

Figure 1:
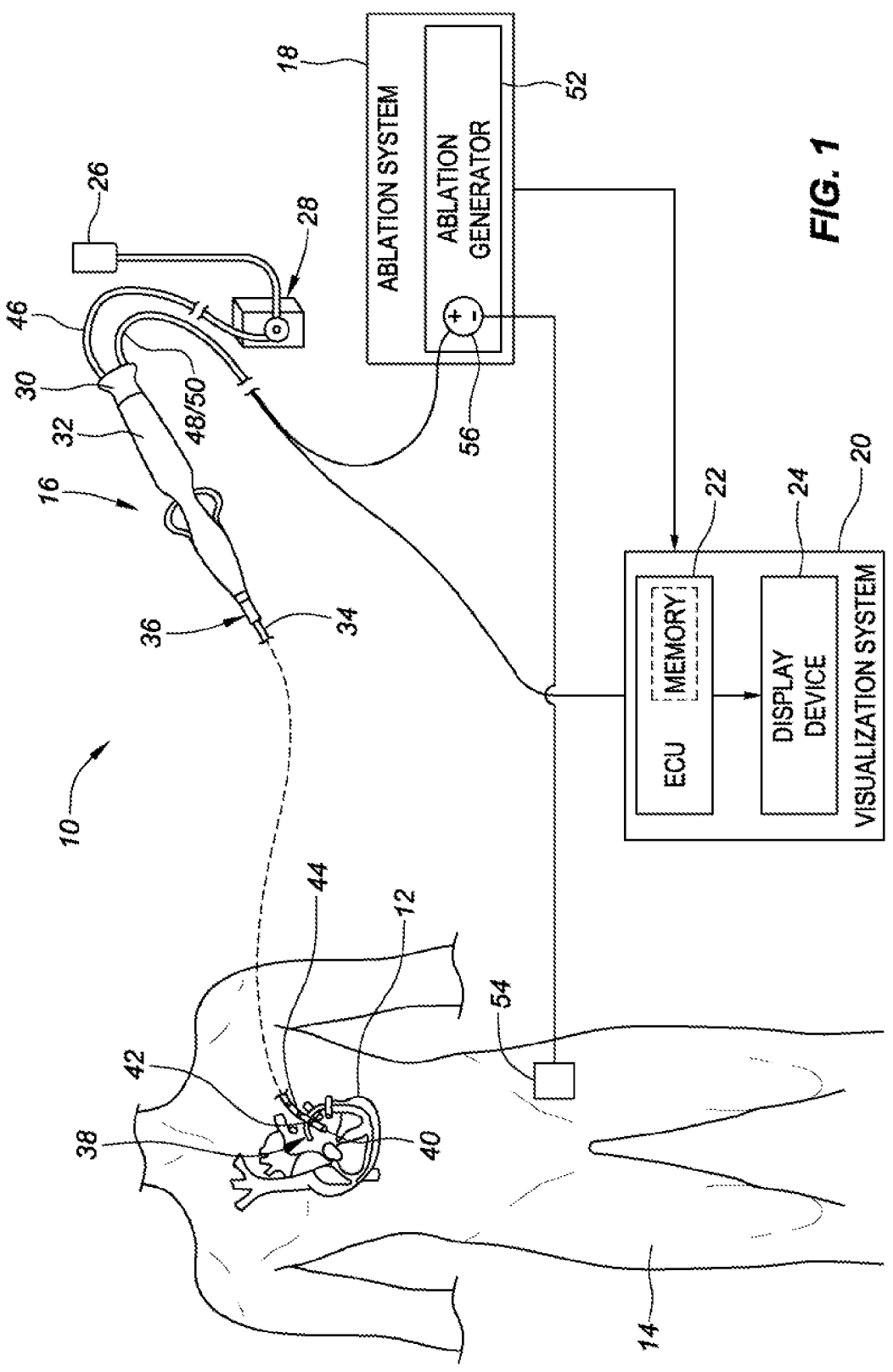
FIG. 1 is a diagrammatic view of a system for performing diagnostic and/or therapeutic functions on cardiac tissue, consistent with various embodiments of the present disclosure.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS OF THE INVENTION

The instant disclosure relates to intravascular catheter apparatus (and systems), and the manufacture thereof; more specifically, aspects of the present disclosure are directed to high-density mapping catheters and to map-ablate catheters for diagnosing and treating cardiac arrhythmias, for example. In particular, the instant disclosure relates to high density mapping/ablation catheters that include high-density mapping electrodes coupled to flexible circuitry which facilitate improved assembly efficacy and cost.

In one embodiment of the present disclosure, a linear electrophysiology ("EP") catheter includes a multi-layer flexible film printed circuit (also referred to as flexible circuitry) with a plurality of (spot) electrodes printed thereon. The flexible circuitry is coupled to a distal tip portion of the catheter. In some specific embodiments, the flexible circuitry may consist of Kapton® (polyimide), polyimide, polyetheretherketone, polyester, polyethylene terephthalate substrate, or a combination thereof. The flexible circuitry includes a plurality of internal electrical traces extending along one or more substrate layers, with the electrodes electrically coupled with at least one of the plurality of electrical traces (through a solder pad, vias, etc.).

The distal tip portion of the catheter shaft may include a trench which facilitates the flush assembly of the flexible circuit to the catheter shaft. This flush mounting of the flexible circuit and electrodes thereon minimizes possible thrombus formation, as well as mechanical irritation of cardiac tissue, for example. Additionally, the resulting smooth outer surface of the catheter shaft assists with passage of the catheter through an introducer (especially the hemostasis valve). Moreover, unlike prior art linear EP catheters which utilize ring electrodes, the catheter shaft of the present embodiment does not require apertures extending through the catheter shaft at each of the electrodes to facilitate communicative coupling with lead wires-which otherwise increase the potential for fluid ingress into a lumen of the catheter.

To facilitate biocompatibility of the flexible circuitry, the flexible circuitry may be plated/coated with a biocompatible material, such as gold. Overall size, width, pitch of the flexible circuitry may vary depending upon the given application.

The trench, in some embodiments, may be helically cut into an outer surface of the catheter shaft, and the flexible circuitry helically wound therein. Various known machining methodologies for forming the trench may be readily applied. For example, laser deposition may be utilized to remove material from the catheter shaft to form the trench which facilitates a width and thickness of the flexible circuitry. Alternatively, the trench may be machined, molded, reflowed, etc. During assembly of the catheter, the flexible circuit may be wound about the catheter shaft and coupled to the shaft within the trench utilizing adhesive, reflow, or other well-known coupling mechanisms. A distal most portion of the flexible circuit may be sandwiched between the catheter shaft and a distal tip of the catheter. In some embodiments, where the distal tip includes additional electrodes, the additional electrodes may be electrically coupled to the flexible circuit to facilitate communication of signals from the additional, distal tip electrodes to a proximal end of the catheter shaft. The distal most portion of the flexible circuit may enter an interior lumen of the catheter shaft at a bond between the catheter shaft and the distal tip. The flexible circuitry may then extend proximally to the handle, where electrical traces which extend from each of the electrodes terminate at an electrical connector. Such embodiments greatly reduce assembly complexity.

Aspects of the present disclosure are further directed to the use of spot electrodes, which often have smaller surface area then a ring electrode which circumferentially extends around a catheter shaft. Accordingly, spot electrodes have an inherent directionality and sensitivity. To mitigate the directionality and sensitivity of the spot electrodes in some embodiments, a distal tip of the EP catheter may include two flexible circuits which extend about the catheter shaft in a double helix arrangement or a single flexible circuit wound up and down the shaft twice. In such an embodiment, pairs of electrodes are positioned on the catheter shaft at equivalent longitudinal position, but radially offset about the longitudinal axis by approximately 180 degrees. While in some applications, electrode directionality may not be desirable; in others, sensing directionality of a wave front may be desirable to improve diagnosis and/or ablation therapy strategy.

Benefits of the present embodiment include lower cost and faster assembly as electrode stringing and electrode adhesive trimming are essentially eliminated. The use of spot electrodes instead of platinum (or platinum-iridium alloy) ring electrodes also reduces assembly cost. Moreover, in use, such an electrophysiology catheter limits the potential for thrombus formation as the contact surface of the spot electrodes are flush with an outer surface of the catheter shaft. Tight tolerance control of the trench depth on the catheter shaft may be critical to preventing thrombus when an ablation therapy is conducted by the EP catheter. The flush arrangement of the spot electrodes further facilitates a low potential for mechanical cardiac irritation. As the relative position of the electrodes along the catheter shaft are known by virtue of the pitch of the spiral and the linear spacing between each of the electrodes along the flexible circuit in some embodiments, more advanced implementations may utilize orientation independent sensing/omnipolar technology ("OIS/OT") and related algorithms. OIS/OT and related algorithms are discussed in more detail in U.S. provisional application No. 61/944,426, filed 25 Feb. 2014, U.S. application Ser. No. 15/118,522, filed 25 Feb. 2015, and international application no. PCT/US2014/011940, filed 16 Jan. 2014, which are hereby incorporated by referenced as though fully disclosed herein.

Known spacing between adjacent electrodes in an array (in two or more directions) facilitates simplified and robust OIS/OT assessments of orientation-specific electrical characteristics of myocardial tissue, for example. In some embodiments, known spacing permits 2-directional assessments of electrical activation direction and maximum voltage amplitude of sampled tissue. Moreover, known electrode spacing allows for the use of diagonal bipole pairs. Two diagonal bipole pairs, which are orthogonal relative to each other, measure the electrical characteristics of the same tissue region. The variation in readings between the orthogonal bipole pairs may be attributed to orientation-specific electrical characteristics of the contacted tissue. Embodiments of the present disclosure may further facilitate reduced complexity decimation by skipping intermediate electrodes, and forming bipole pairs with larger electrode spacing configurations than created by adjacent electrodes in the array. Decimation may be used to determine electrical characteristics of tissue at a less granular resolution. Further, a clinician may assess situational performance of the planar array at various bipole spacings. In various embodiments consistent with the present disclosure, adjacent bipole pairs may have various spacings, and be oriented in such a way as to facilitate various spatial orientations relative to one another.

The benefits of known electrode spacing along two or more perpendicular directions include a simplified computation of the electric field vector based only on average bipole voltages in the x, y directions. Known electrode spacing may also facilitate OIS/OT-methods that generate bipolar electrogram signals at various orientations with respect to wavefronts, so that a clinician may employ arbitrary catheter orientations (as discussed in more detail above). Finally, the known electrode spacing of the array facilitates a balanced and integrated view of voltage, fractionation, and/or activation patterns, which may be readily sampled from adjacent electrodes with known spacing. This information may then be used to compute a divergence and curl (i.e., to detect/locate foci and rotor cores from activation directions).

Various embodiments of the present disclosure are directed to EP mapping catheters, ablation catheters, and combinations thereof. In an example ablation catheter, a tip electrode may be communicatively coupled to controller circuitry via a dedicated lead wire, or integrated into a flexible circuit as a dedicated trace thereon. In some embodiments, an additional flexible circuit layer may be required for a wide trace which carries a desired ablation current with minimal/acceptable losses. In yet other implementations, a distal tip electrode may utilize an independent lead wire to deliver current for ablation therapy, but utilize a trace on the flexible circuit for sensing purposes (e.g., measuring electrograms or impedance).

In some simplified embodiments of the present disclosure, a trench need not be formed in an outer surface of the catheter shaft. Instead, the flexible circuit may be applied directly onto the outer surface of the catheter shaft, and heat-shrink tubing applied over the assembly. The reflow process of the heat-shrink tubing will (partially) compress the flexible circuit into the outer surface of the catheter shaft. To improve overall adhesion of the assembly, some specific embodiments may utilize polyurethane for the substrate of the flexible circuit (instead of, for example, polyimide), a base compound of Pebax® tubing (one type of heat-shrink tubing). Moreover, Pebax® is a common compound used for cardiac catheter shafts-further improving overall adhesion of the assembly. In such embodiments, it may still be desirable to have pre-formed grooves within the catheter shaft to facilitate improved placement of the flexible circuit along the catheter shaft. The pre-formed grooves correct for the majority of the depth adjustment between the spot electrodes and the outer surface of the catheter shaft, and reflow of the heat-shrink tubing corrects any slight height variations between the spot electrodes and the catheter shaft along the trench.

In yet other simplified embodiments of the present disclosure, flexible circuitry, including spot electrodes, may be directly coupled to a catheter shaft (absent a trench) via a reflow process and/or adhesive application.

Aspects of the present disclosure may further be applied to basket catheters, with one or more of the splines of the basket including flexible circuits, with spot electrodes mounted thereon, being helically wrapped around the splines. Such an embodiment facilitates the use of cylindrical splines which are less likely to cause trauma when moved within a cardiovascular system of the patient.

Referring now to the drawings wherein like reference numerals are used to identify identical components in the various views, FIG. 1 illustrates one example embodiment of a system 10 for performing one or more diagnostic and/or therapeutic functions in association with cardiac muscle 12 within a human body 14. It should be understood, however, that the system 10 may find application in connection with the ablation of a variety of other tissues within human and non-human bodies.

The system 10 may include a medical device (such as, for example, an electrophysiology catheter 16), an ablation system 18, and/or a system 20 for the visualization, navigation, and/or mapping of internal body structures. The system 20 may include, for example and without limitation, an electronic control unit (ECU) 22 and a display device 24. Alternatively, the ECU 22 and/or the display 24 may be separate and distinct from, but electrically connected to and configured for communication with, the system 20.

With continued reference to FIG. 1, the catheter 16 can be provided for examination, diagnosis, and/or treatment of internal body tissues such as within a cardiac muscle 12. In an example embodiment, the electrophysiology catheter 16 is a diagnostic catheter, such as a non-contact mapping catheter that may include a plurality of electrodes configured to monitor one or more electrical signals transmitted throughout the adjacent cardiac tissue. For example, electrophysiology catheter 16 may comprise a linear ablation catheter. The ablation catheter may be irrigated in an embodiment such that the catheter 16 may further comprise an inner fluid delivery tubing that may include at least one fluid delivery port. In the present embodiment, wherein the catheter 16 is an irrigated catheter, the catheter 16 can be connected to a fluid source 26 providing a biocompatible fluid such as saline, or a medicament, through a pump 28 (which may comprise, for example, a fixed rate roller pump or variable volume syringe pump with a gravity feed supply from the fluid source 26, as shown) for irrigation. It should be understood, however, that catheter 16 is not limited to a linear ablation catheter and is not limited to an irrigated catheter. Rather, in other embodiments, the catheter 16 may comprise an ablation catheter (e.g., radio frequency (RF), cryoablation, ultrasound, etc.), a mapping catheter, or a combination thereof. The catheter may be configured with or without irrigation.

In one example embodiment where the catheter comprises an ablation catheter, the catheter 16 is electrically connected to the ablation system 18 to allow for the delivery of ablative energy, or the like. The catheter 16 may include a cable connector or interface 30, a handle 32, a shaft 34 having a proximal end 36 and a distal end 38, and one or more electrodes 40, 42 mounted in or on the shaft 34 of the distal portion of catheter 16. In an example embodiment, the electrodes 40, 42 are disposed at or near the distal end 38 of the shaft 34, with the electrode(s) 40 comprising an ablation electrode disposed at the extreme distal end portion 38 of the shaft 34 (i.e., tip electrode 40), and the electrode(s) 42 comprising a spot electrode used, for example, with the visualization, navigation, and EP mapping system 20. Spot electrode(s) 42 can be configured to provide a signal indicative of both a position and orientation of at least a portion of the catheter 16. The catheter 16 may further include other conventional components such as, for example and without limitation, a temperature sensor (or sensors) 44, additional electrodes, and corresponding conductors.

The connector 30 provides mechanical, fluid, and electrical connection(s) for cables 46, 48, 50 extending from the pump 28, the ablation system 18, and the visualization, navigation, and/or mapping system 20. The connector 30 is conventional in the art and is disposed at the proximal end 36 of the catheter 16.

The handle 32 provides a location for the clinician to hold the catheter 16 and may further provide means for steering or guiding the shaft 34 within the body 14 as known in the art. Catheter handles 32 are generally conventional in the art and it will be understood that the construction of the handle 32 may vary. In an embodiment, for the purpose of steering the shaft 34 within the body 14, the handle 32 can be substituted by a controllable robotic actuator.

The shaft 34 is an elongate, tubular, flexible member configured for movement within the body 14. The shaft 34 supports, for example and without limitation, one or more electrodes (e.g., electrodes 40, 42), associated conductors, and possibly additional electronics used for signal processing, visualization, localization, and/or conditioning. The shaft 34 may also permit transport, delivery and/or removal of fluids (including irrigation fluids, medicaments, and bodily fluids, etc.), medicines, and/or surgical tools or instruments. The shaft 34 can include one or more lumens configured to house and/or transport electrical conductors, fluids, or surgical tools. The shaft 34 can be introduced into a blood vessel or other structure within the body 14 through a conventional introducer. The shaft 34 is then steered or guided through the body 14 to a desired location such as the tissue 12 with pullwires, tension elements, so-called push elements, or other means known in the art.

As generally illustrated in FIG. 1, an ablation system 18 can be comprised of, for example, an ablation generator 52 and one or more ablation patch electrodes 54. The ablation generator 52 generates, delivers, and controls ablation energy (e.g., radio-frequency) output by the ablation catheter 16 and the tip electrode 40 thereof, in particular. The generator 52 is conventional in the art and may comprise a commercially available unit sold under the model Ampere Cardiac Ablation Generator, available from Abbott Medical Systems. In one embodiment, the generator 52 may include an RF ablation signal source 56 configured to generate an ablation signal that is output across a pair of source connectors: a positive polarity connector SOURCE (+), which electrically connects to the tip electrode 40 of the catheter 16; and a negative polarity connector SOURCE (−), can be electrically connected to one or more of the patch electrodes 54. It should be understood that the term connectors as used herein does not imply a particular type of physical interface mechanism, but is rather broadly contemplated to represent one or more electrical nodes (including multiplexed and de-multiplexed nodes). The source 56 is configured to generate a signal at a predetermined frequency in accordance with one or more user specified control parameters (e.g., power, time, etc.) and under the control of various feedback sensing and control circuitry. The source 56 may generate a signal, for example, with a frequency of about 450 kHz or greater for RF energy. The generator 52 may also monitor various parameters associated with the ablation procedure including, for example, impedance, the temperature at the distal tip of the catheter, applied ablation energy, power, force, proximity, and the position of the catheter, and provide feedback to the clinician or another component within the system 10 regarding these parameters.

The visualization, navigation, and/or EP mapping system 20 with which the electrodes 42 can be used may comprise an electric field-based system, such as, for example, ENSITE NAVX (aka EnSite Classic as well as newer versions of the EnSite system, denoted as ENSITE VELOCITY) and commercially available from Abbott Medical Systems and as generally shown with reference to U.S. Pat. No. 7,263,397 titled "Method and Apparatus for Catheter Navigation and Location and Mapping in the Heart," the entire disclosure of which is incorporated herein by reference. In accordance with an electric field-based system, the positioning electrode(s) 42 can be configured to be responsive to an electric field transmitted within the body of the patient. The electrode(s) 42 can be used to sense an impedance at a particular location and transmit a representative signal to an external computer or processor. In other embodiments, however, the visualization, navigation, and/or mapping system may comprise other types of systems, such as, for example and without limitation: a magnetic field-based system such as the CARTO System available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd. of Haifa, Israel (now owned by Abbott Medical Systems), and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference. In accordance with a magnetic field-based system, the electrode(s) 42 can be configured to be responsive to a magnetic field transmitted through the body of the patient. The electrode(s) 42 can be used to sense the strength of the field at a particular location and transmit a representative signal to an external computer or processor. The electrode(s) 42 may comprise one or more metallic coils located on or within the catheter 16 in a magnetic field-based system. Alternatively, a combination electric field-based and magnetic field-based system such as the CARTO 3 System also available from Biosense Webster, and as generally shown with reference to U.S. Pat. No. 7,536,218 entitled "Hybrid Magnetic-Based and Impedance-Based Position Sensing," the entire disclosure of which is incorporated herein by reference, may be used. In accordance with a combination electric field-based and magnetic field-based system, the electrodes 42 may comprise both one or more impedance-based electrodes and one or more magnetic coils. Commonly available fluoroscopic, computed tomography (CT), and magnetic resonance imaging (MRI)-based systems can also be used to facilitate visualization and navigation.

Figure 2:
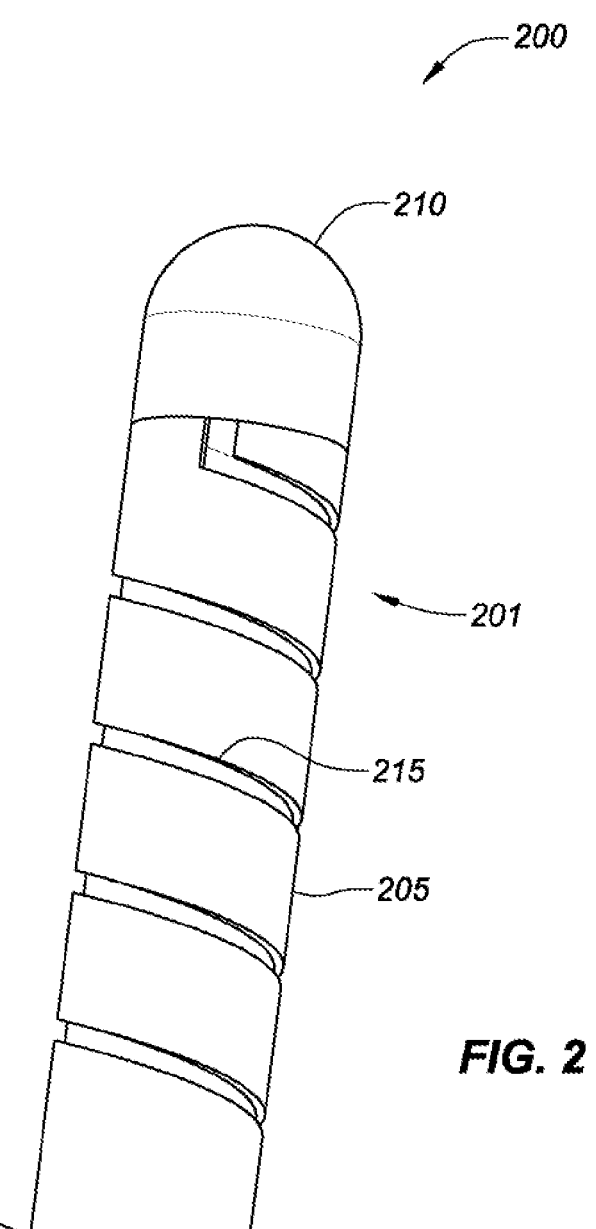
FIG. 2 is an isometric front view of a partially-assembled electrophysiology catheter tip, consistent with various embodiments of the present disclosure.
Figure 4:
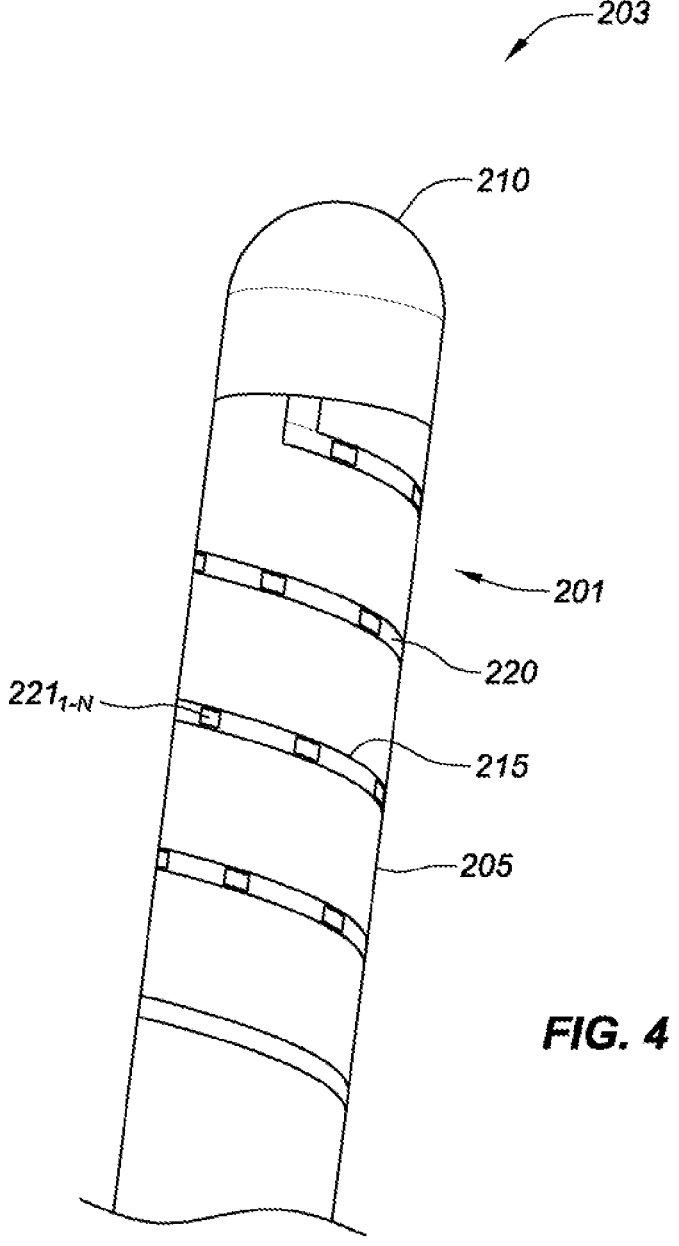
FIG. 4 is an isometric front view of an assembled electrophysiology catheter tip, consistent with various embodiments of the present disclosure.

FIG. 2 is an isometric front view of a partially-assembled electrophysiology catheter tip portion 200, consistent with various embodiments of the present disclosure. The partially-assembled electrophysiology catheter tip portion 200 includes a catheter shaft 201 with a helical trench 215 cut into an outer surface 205 of a distal portion of the catheter shaft. The depth and width of the trench facilitates placement of a flexible circuit including spot electrodes thereon (as shown in FIG. 4). In some embodiments, the sensing surface of the spot electrodes is approximately flush with the outer surface 205 of the catheter shaft 201.

The catheter shaft 201 is coupled at a distal end to distal cap 210 (also referred to as a distal tip). The distal cap may be a non-traumatic tip via rounds thereon. The distal cap 210 may be coupled to the catheter shaft 201 using known methods, such as a press fit, adhesive, laser welding, ultrasonic, welding, among other known coupling techniques.

Figure 3:
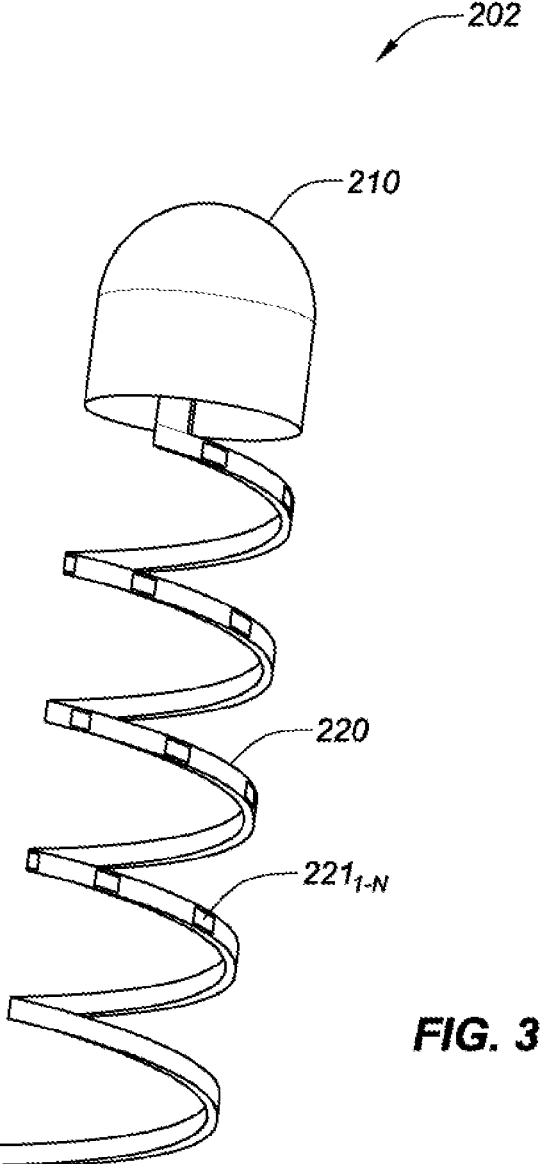
FIG. 3 is an isometric front view of a partially-assembled electrophysiology catheter tip, consistent with various embodiments of the present disclosure.

FIG. 3 is an isometric front view of a partially-assembled electrophysiology catheter tip portion 202, consistent with various embodiments of the present disclosure. The partially-assembled electrophysiology catheter tip portion 202 includes a flexible circuit 220 with a plurality of spot electrodes $221_{1-N}$ thereon, and a distal cap 210 coupled to a distal end of the flexible circuit 220. The partially-assembled electrophysiology catheter tip portion 202 may be a sub-assembly that is prepared prior to final assembly of the electrophysiology catheter.

While FIG. 3 shows spot electrodes $221_{1-N}$ being evenly distributed along a length of the flexible circuit 220, various applications of the present application may utilize uneven electrode distributions or weighted distributions. For example, in some embodiments, it may be desirable to have a higher density of electrodes closer to the distal cap 210 of the catheter with a progressively smaller density of electrodes extending proximally. Moreover, as discussed above, in some embodiments it may be desirable to have a number of electrodes radially positioned about the catheter shaft at one or more longitudinal positions along the catheter shaft. In such an application, a single flexible circuit may be helically wound about the catheter shaft, two or more times, to position radially offset electrodes along the catheter shaft. Alternatively, or in addition, two or more distinct flexible circuits may be helically wrapped about the catheter shaft (e.g., in a double-helix fashion) to facilitate desired radial offsets of the electrodes. In yet other embodiments, a single flexible circuit may be wrapped entirely about a distal portion of the catheter shaft to facilitate numerous electrode configurations both radially and longitudinally along the shaft. In yet further embodiments, a wide-band flexible circuit may be helically wrapped about the catheter shaft with electrodes offset along a length and width of the flexible circuit to facilitate at least some radial offset of electrodes when assembled to the catheter shaft (see, e.g., FIGS. 9A-10B).

FIG. 4 is an isometric front view of an assembled electrophysiology catheter tip 203, consistent with various embodiments of the present disclosure. The assembled electrophysiology catheter tip portion 203 includes a catheter shaft 201, distal cap 210, and flexible circuit 220. As discussed in reference to FIGS. 2 and 3, the flexible circuit 220 is inserted into a helical trench 215 extending into an outer surface 205 of the catheter shaft. The depth of the trench, for some applications, may facilitate a plurality of electrodes $221_{1-N}$, extending along a length of the flexible circuit, and being flush with or extending above the outer surface 205 of the shaft (for contact-type electrodes) or below the outer surface of the shaft (for non-contact-type electrodes). Further, in some embodiments, an additional biocompatible layer may be assembled over the electrophysiology catheter tip 203, and reflowed to prevent ingress of bodily fluids into the catheter and to mitigate sharp edges which may result in thrombus formation. In some applications, laser etching may be used to remove the biocompatible layer from above the electrodes (which may already comprise a biocompatible material, or be plated, i.e., gold plated).

When assembled, a distal end of flexible circuit 220 may extend into a lumen of the catheter shaft at the joint between catheter shaft 201 and distal cap 210. The flexible circuit may then be electrically coupled to lead wires which extend a length of the catheter shaft, or extend itself to a proximal end of the catheter shaft. An electrical connector at a proximal end of the catheter may then complete an electrical circuit between controller circuitry and electrodes $221_{1-N}$.

To facilitate traditional printed circuit technology, the flexible circuits may be printed on a flat panel, with turns for where the flexible circuit will enter a lumen in the catheter shaft. The flat flexible circuit may then be wrapped around the catheter shaft to form the desired helical shape. Moreover, to facilitate long flexible circuits which are capable of extending a length of a catheter shaft (often 48" or longer), whereas existing printed circuit panel sizes are limited to 24", the flexible circuit may be printed on the panel in a serpentine fashion and folded during assembly to achieve the desired lengths.

FIG. 5A is a side view, and FIG. 5B is a cross-sectional front view, of an electrophysiology catheter tip 500, consistent with various embodiments of the present disclosure. As shown in FIGS. 5A-B, the catheter tip 500 includes a catheter shaft 505 which distally extends to a distal cap 510. A plurality of electrodes $521_{1-N}$ are distributed radially and longitudinally about the catheter shaft 505. In the present embodiment, 4 electrodes are radially distributed around the catheter shaft (as shown in FIG. 5B) at each of planes $522_{1-6}$. Each of the planes are positioned trans-axial relative to a longitudinal axis of the catheter shaft. As in various embodiments disclosed herein, such an electrode pattern may be implemented on the catheter shaft using one or more flexible circuits which are applied to the catheter shaft or otherwise integrated onto the catheter shaft itself. For example, through the application of conductive and non-conductive, and biocompatible layers on the catheter shaft itself.

FIG. 6A is a side view and FIG. 6B is a cross-sectional front view of an electrophysiology catheter tip 600, consistent with various embodiments of the present disclosure. As shown in FIGS. 6A-B, the catheter tip 600 includes a catheter shaft 605 which extends distally to a distal cap 610. A plurality of electrodes $621_{1-10}$ are distributed radially and longitudinally about the catheter shaft 605. In the present embodiment, 2 electrodes are radially distributed about the catheter shaft (as shown in FIG. 6B) at each of planes 62216. Each of the planes are positioned trans-axial relative to a longitudinal axis of the catheter shaft. The positioning of the electrodes at each respective plane are radially offset relative to electrodes on adjacent planes. As shown herein, the radial offset of electrodes at adjacent planes is approximately 180 degrees, though other embodiments are readily envisioned including 90 degrees, 270 degrees, etc. As in various embodiments disclosed herein, such an electrode pattern may be implemented on the catheter shaft using one or more flexible circuits which are applied to the catheter shaft or otherwise integrated onto the catheter shaft itself.

One particular advantage of the embodiment of FIGS. 6A-B is in regard to neutral surfaces (as discussed in more detail below). As the electrode pattern forms a T-shape along the surface of the catheter shaft, in response to steering inputs on the catheter shaft, the change in relative positioning of the electrodes due to the deflection of the catheter is minimal. This is particularly desirable in EP catheter applications utilizing OIS/OT algorithms which are dependent on known/fixed/predicable spacing of the electrodes for electrophysiology mapping, among other cardiac diagnostics.

In reference to the embodiments disclosed in FIGS. 5A-6B the catheter shaft 505/605 may transition between deflected and undeflected states. As shown in FIGS. 6A-B, electrodes may be distributed along a longitudinal axis of the catheter shaft 605 (e.g., $621_{10}$ and $621_8$). In the present embodiment the electrodes $621_{1-10}$ are spot electrodes. In other embodiments, the catheter shaft can comprise a number of various quantities of electrodes. In yet other embodiments, the one or more electrodes disposed on the catheter shaft may comprise ring electrodes that extend (partially) around an outer circumference of the catheter shaft. In another embodiment, a ring electrode can be coupled to a portion of a conductor that is exposed to an exterior portion of the catheter shaft (i.e., solder pad on the flexible circuit). The ring electrode can comprise a composition that would be known to one of ordinary skill in the art and can be swaged, secured with adhesive, or otherwise coupled to the catheter shaft so that the ring is electrically coupled to the conductor. In yet other embodiments, the one or more electrodes can comprise electrodes that extend around a portion of an outer circumference of the shaft, or can comprise spot electrodes of different shapes and sizes than those illustrated in FIGS. 5A-6B. In yet another embodiment, the electrode can comprise a tab that is wrapped around an outer circumference of the catheter shaft and coupled thereto. In various embodiments, the tab may be configured to extend around the entire circumference or a partial circumference of an outer surface of the catheter shaft. The tab can comprise an electrically conductive material that has been added on to a base layer. While the illustrated embodiments show electrodes evenly spaced along the catheter shaft, in other embodiments the electrodes can be placed at various positions both axial and radial about the catheter shaft. By placing the electrodes at various axial and radial positions, separate and unique three-dimensional locations in space may be achieved and utilized as a centerline of the medical device for visualization in an imaging system, for example. Moreover, such an electrode configuration facilitates a neutral plane along a length of the catheter shaft with known and consistent catheter steering properties.

While the flexible circuits, and traces thereon, that communicatively couple electrodes $521_{1-N}/621_{1-10}$ with controller circuitry at a proximal end of the catheter are not shown in FIGS. 5A-6B, the flexible circuits may be coupled to an exterior portion of catheter shaft 605 (as discussed throughout) or alternatively a portion of the catheter shaft may comprise a conductive material (e.g., traces) which extend proximally along the length of the catheter shaft. Once the electrodes are coupled to the traces, an insulative/bio-compatible material may be applied to the conductive material. To facilitate desirable steering characteristics, the traces and/or the flexible circuitry as a whole may run along a neutral plane of the shaft. The neutral plane of the catheter shaft can comprise a location along an outer diameter of the shaft that is approximately the same distance, in each direction, from a pullwire.

FIG. 7A is an isometric front view of an assembled electrophysiology catheter tip 700, and FIG. 7B is an isometric front view of a partially-assembled electrophysiology catheter tip 702 of FIG. 7A. As shown in FIGS. 7A-B, the electrophysiology catheter tip includes a catheter shaft 701 coupled at a distal end to a distal cap 710, and flexible circuit 720. The flexible circuit includes both a helically extending portion 723 which extends longitudinally and helically about the catheter shaft 701, and a laterally extending portion 722 which extends about a majority of the catheter shaft circumference. The helically extending portion 723 includes a plurality of electrical traces that may be sandwiched between one or more circuit board layers of the flexible circuit, and which deliver electrical signals between a plurality of electrodes $721_{1-N}$ and controller circuitry at a proximal end of the catheter shaft. The laterally extending portion 722 includes the plurality of electrodes $721_{1-N}$ which may be (un) evenly distributed about the circumference of the catheter shaft 701. The plurality of electrodes $721_{1-N}$ may be positioned on an outer surface of the flexible circuit to facilitate contact based electrophysiology sensing, positioned in a non-contact electrophysiology sensing manner by placing the electrodes beneath one or more layers of the flexible circuit, or a combination thereof. While the present embodiment depicts a single laterally extending portion 722, two or more laterally extending portions are readily envisioned.

The flexible circuit 720 may be inserted into a helically and laterally extending trench which extends into an outer surface of the catheter shaft 701. The depth of the trench for some applications may facilitate a plurality of electrodes 721$_{1-N}$, extending along a length of the flexible circuit, to be flush or to extend above an outer surface of the shaft (for contact-type electrodes) or below the outer surface of the shaft (for non-contact-type electrodes). Further, in some embodiments, an additional biocompatible layer may be assembled over the assembled electrophysiology catheter tip 700 and reflowed to prevent ingress of bodily fluids into the catheter and to mitigate sharp edges which may result in thrombus formation. In some applications, laser etching may be used to remove the biocompatible layer from above the electrodes (which may already comprise a biocompatible material, or be plated with a biocompatible layer, i.e., gold plated).

When assembled, a distal end of flexible circuit 720 may extend into a lumen of the catheter shaft at a joint between catheter shaft 701 and distal cap 710. The flexible circuit may then be electrically coupled to lead wires which extend a length of the catheter shaft, or extend itself to a proximal end of the catheter shaft. An electrical connector at a proximal end of the catheter may then complete an electrical circuit between controller circuitry and electrodes 721$_{1-N}$.

FIG. 8A is an isometric front view of an assembled electrophysiology catheter tip 800, consistent with various embodiments of the present disclosure, and FIG. 8B is an isometric front view of a partially-assembled electrophysiology catheter tip 802 of FIG. 8A. As shown in FIGS. 8A-B, the electrophysiology catheter tip includes a catheter shaft 801 coupled at a distal end to a distal cap 810, and flexible circuit 820. The flexible circuit includes both a helically extending portion 823 which extends longitudinally and helically about the catheter shaft 801, and a laterally extending portion 822 which extends about a small portion of the catheter shaft circumference (approximately one quarter of the circumference of the catheter shaft). The helically extending portion 823 includes a plurality of electrical traces that may be sandwiched between one or more circuit board layers of the flexible circuit, and which deliver electrical signals between a plurality of electrodes 821$_{1-N}$ and controller circuitry at a proximal end of the catheter shaft. The laterally extending portion 822 includes the plurality of electrodes 821$_{1-N}$ which may be (un) evenly distributed about the circumference of the catheter shaft 801. The plurality of electrodes 821$_{1-N}$ may be positioned on an outer surface of the flexible circuit to facilitate contact based electrophysiology sensing, positioned in a non-contact electrophysiology sensing manner by placing the electrodes beneath one or more layers of the flexible circuit, or a combination thereof. While the present embodiment depicts a single laterally extending portion, two or more laterally extending portions are readily envisioned. Furthermore, while the present embodiments depicts two electrodes, one or more electrodes are readily envisioned.

The flexible circuit 820 may be inserted into a helically and laterally extending trench which extends into an outer surface of the catheter shaft 801. The depth of the trench for some applications may facilitate a plurality of electrodes 821$_{1-N}$, extending along a length of the flexible circuit, to be flush or extending above an outer surface of the shaft (for contact-type electrodes) or below the outer surface of the shaft (for non-contact-type electrodes).

When assembled, a distal end of flexible circuit 820 may extend into a lumen of the catheter shaft at the joint between catheter shaft 801 and distal cap 810. The flexible circuit may then be electrically coupled to lead wires which extend a length of the catheter shaft, or extend itself to a proximal end of the catheter shaft. An electrical connector at a proximal end of the catheter may then complete an electrical circuit between controller circuitry and electrodes 821$_{1-N}$.

FIG. 9A is an isometric front view of an assembled electrophysiology catheter tip 900, and FIG. 9B is an isometric front view of a partially-assembled electrophysiology catheter tip 902 of FIG. 9A. As shown in FIGS. 9A-B, the electrophysiology catheter tip includes a catheter shaft 901 coupled at a distal end to a distal cap 910, and flexible circuit 920. The flexible circuit includes both a helically extending portion 923 which extends longitudinally and helically about the catheter shaft 901, and laterally extending portions 922$_{1-3}$ which extend about a majority of the catheter shaft circumference. The helically extending portion 923 includes a plurality of electrical traces that may be sandwiched between one or more circuit board layers of the flexible circuit, and which deliver electrical signals between a plurality of electrodes 921$_{1-N}$ and controller circuitry at a proximal end of the catheter shaft. The laterally extending portions 922$_{1-3}$ include the plurality of electrodes 921$_{1-N}$ which may be (un) evenly distributed about the circumference of the catheter shaft 901. The plurality of electrodes 921$_{1-N}$ may be positioned on an outer surface of the flexible circuit to facilitate contact based electrophysiology sensing, positioned in a non-contact electrophysiology sensing manner by placing the electrodes beneath one or more layers of the flexible circuit, or a combination thereof. While the present embodiment depicts three laterally extending portions, one or more laterally extending portions are readily envisioned, depending on the resolution granularity desired for a given electrophysiology mapping application.

The flexible circuit 920 may be inserted into a helically and laterally extending trench which extends into an outer surface of the catheter shaft 901. The depth of the trench for some applications may facilitate a plurality of electrodes 921$_{1-N}$, extending along a length of the flexible circuit, to be flush, extend above an outer surface of the shaft (for contact-type electrodes), or extend below the outer surface of the shaft (for non-contact-type electrodes). Further, in some embodiments, an additional biocompatible layer may be assembled over the assembled electrophysiology catheter tip 900 and reflowed to prevent ingress of bodily fluids into the catheter and to mitigate sharp edges which may result in thrombus formation. In some applications, laser etching may be used to remove the biocompatible layer from above the electrodes (which may already comprise a biocompatible material, or plated biocompatible material, i.e., gold plated).

As shown in FIGS. 9A-B, three laterally extending portions 922$_{1-3}$ are distributed about a length of the catheter shaft 901. The placement of the electrodes 921$_{1-N}$ radially about the catheter shaft may facilitate alignment, or as shown in FIGS. 9A-B, a radially offset arrangement between longitudinally adjacent electrodes.

While in FIGS. 9A-B, three laterally extending portions 922 are shown, a skilled artisan will appreciate that various numbers of laterally extending portions may be distributed along a length of the catheter shaft 901. Moreover, the distribution of the laterally extending portions may not necessarily be regular, but instead placement of the laterally extending portion may be weighted to locations along the catheter shaft where enhanced resolution electrophysiology mapping is desirable (e.g., near a distal tip 910 of the catheter shaft 901).

When assembled, a distal end of flexible circuit 920 may extend into a lumen of the catheter shaft at the joint between catheter shaft 901 and distal cap 910. The flexible circuit may then be electrically coupled to lead wires which extend a length of the catheter shaft, or extend itself to a proximal end of the catheter shaft. An electrical connector at a proximal end of the catheter may then complete an electrical circuit between controller circuitry and electrodes $921_{1-N}$.

FIG. 10A is an isometric front view of an assembled electrophysiology catheter tip 1000, consistent with various embodiments of the present disclosure, and FIG. 10B is an isometric front view of a partially-assembled electrophysiology catheter tip 1002 of FIG. 10A. As shown in FIGS. 10A-B, the electrophysiology catheter tip includes a catheter shaft 1001 coupled at a distal end to a distal cap 1010, and flexible circuit 1020. The flexible circuit includes both a helically extending portion 1023 which extends longitudinally and helically about the catheter shaft 1001, and laterally extending portions $1022_{1-2}$ which extend about a small portion of the catheter shaft circumference (approximately one quarter of the circumference of the catheter shaft). The helically extending portion 1023 includes a plurality of electrical traces that may be sandwiched between one or more circuit board layers of the flexible circuit, and which deliver electrical signals between a plurality of electrodes $1021_{1-N}$ and controller circuitry at a proximal end of the catheter shaft. The laterally extending portions $1022_{1-2}$ include the plurality of electrodes $1021_{1-N}$ which may be (un) evenly distributed about the circumference of the catheter shaft 1001. The plurality of electrodes $1021_{1-N}$ may be positioned on an outer surface of the flexible circuit to facilitate contact based electrophysiology sensing, positioned in a non-contact electrophysiology sensing manner by placing the electrodes beneath one or more layers of the flexible circuit, or a combination thereof. While the present embodiment depicts a single laterally extending portion, two or more laterally extending portions are readily envisioned. Furthermore, while the present embodiments depicts two electrodes, one or more electrodes are readily envisioned.

The flexible circuit 1020 may be inserted into a helically and laterally extending trench which extends into an outer surface of the catheter shaft 1001. The depth of the trench for some applications may facilitate a plurality of electrodes $1021_{1-N}$, extending along a length of the flexible circuit, to be flush with or extend above an outer surface of the shaft (for contact-type electrodes), or below the outer surface of the shaft (for non-contact-type electrodes).

When assembled, a distal end of flexible circuit 1020 may extend into a lumen of the catheter shaft at the joint between catheter shaft 1001 and distal cap 1010. The flexible circuit may then be electrically coupled to lead wires which extend a length of the catheter shaft, or extend itself to a proximal end of the catheter shaft. An electrical connector at a proximal end of the catheter may then complete an electrical circuit between controller circuitry and electrodes $1021_{1-N}$.

As shown in FIGS. 10A-B, two laterally extending portions $1022_{1-2}$ are distributed about a length of the catheter shaft 1001. The placement of the electrodes $1021_{1-N}$ radially about the catheter shaft may facilitate alignment, or a radially offset arrangement between longitudinally adjacent electrodes.

While in FIGS. 10A-B, two laterally extending portions 1022 are shown, a skilled artisan will appreciate that various numbers of laterally extending portions may be distributed along a length of the catheter shaft 1001. Moreover, the distribution of the laterally extending portions may not necessarily be regular, but instead placement of the laterally extending portion may be weighted to locations along the catheter shaft where enhanced resolution electrophysiology mapping is desirable (e.g., near a distal cap 1010 of the catheter shaft 1001).

In yet other embodiments consistent with FIGS. 7A-10B, laterally extending portion(s) of the flexible circuit may extend from a longitudinally extending portion of the flexible circuit, wrap circumferentially about the entire catheter shaft, and a distal end of the laterally extending portion(s) coupled back to the longitudinally extending portion of the flexible circuit. For example, the distal end of the laterally extending portion may be tucked under the longitudinally extending portion, or may be adhered with adhesive or another coupling mechanism well known in the art.

Various electrode patterns, especially linear electrode patterns extending along a catheter shaft and the use of neutral planes to facilitate improved catheter navigation within an intravascular system are generally shown with reference to PCT Application No. PCT/US2018/014430 titled "Sheath Visualization," the entire disclosure of which is incorporated herein by reference.

While various embodiments discussed herein have been in reference to flexible circuitry, various other embodiments consistent with the present disclosure may utilize various types of stretchy conductors/substrates well known to those skilled in the art.

While aspects of the present disclosure have been presented as being readily applicable to radio-frequency ablation techniques, aspects of the present disclosure are also readily applied to irreversible electroporation (also referred to as direct current ablation). Moreover, while bipolar and monopolar RF techniques have been disclosed herein, variations on such techniques are also envisioned. For example, a bipolar ablation configuration may include alternating adjacent electrode polarities on the electrode array with the ground pad having a negative polarization. In one monopolar ablation configuration, the ground pad may have an alternating polarity over time, with adjacent electrodes carrying alternating polarities. Further, aspects of the present disclosure have been discussed including diagnosis and treatment of cardiac arrhythmias (e.g., atrial fibrillation); however, the present disclosure is readily applicable to the diagnosis and treatment of a number of different ailments, for example, Brugada syndrome.

Yet further embodiments consistent with the present disclosure may be directed to high-voltage direct current ("DC") ablation (either bi-polar or mono-polar configuration). In such embodiments the high-voltage DC may include voltages between 400 and 4,000 Volts, and minimized current draw to target a voltage gradient rather than current delivery.

U.S. provisional application No. 62/414,634, filed 28 Oct. 2016, U.S. provisional application No. 62/572,186, filed 13 Oct. 2017, and U.S. application Ser. No. 15/793,093, filed 25 Oct. 2017 are all generally directed to flexible, high-density mapping catheters and are incorporated by reference as though fully set forth herein.

While various embodiments of high-density electrode catheters are disclosed herein, the teachings of the present disclosure may be readily applied to various other catheter embodiments as disclosed, for example, in the following patents and patent applications which are hereby incorporated by reference: U.S. provisional application No. 61/753, 429, filed 16 Jan. 2013; U.S. provisional application No. 60/939,799, filed 23 May 2007; U.S. application Ser. No. 11/853,759 filed 11 Sep. 2007, now U.S. Pat. No. 8,187,267, issued 29 May 2012; U.S. provisional application No. 60/947,791, filed 3 Jul. 2007; U.S. application Ser. No.

12/167,736, filed 3 Jul. 2008, now U.S. Pat. No. 8,206,404, issued 26 Jun. 2012; U.S. application Ser. No. 12/667,338, filed 20 Jan. 2011 (371 date), published as U.S. patent application publication no. US 2011/0118582 A1; U.S. application Ser. No. 12/651,074, filed 31 Dec. 2009, published as U.S. patent application publication no. US 2010/0152731 A1; U.S. application Ser. No. 12/436,977, filed 7 May 2009, published as U.S. patent application publication no. US 2010/0286684 A1; U.S. application Ser. No. 12/723,110, filed 12 Mar. 2010, published as U.S. patent application publication no. US 2010/0174177 A1; U.S. provisional application No. 61/355,242, filed 16 Jun. 2010; U.S. application Ser. No. 12/982,715, filed 30 Dec. 2010, published as U.S. patent application publication no. US 2011/0288392 A1; U.S. application Ser. No. 13/159,446, filed 14 Jun. 2011, published as U.S. patent application publication no. US 2011/0313417 A1; international application no. PCT/US2011/040629, filed 16 Jun. 2011, published as international publication no. WO 2011/159861 A2; U.S. application Ser. No. 13/162,392, filed 16 Jun. 2011, published as U.S. patent application publication no. US 2012/0010490 A1; U.S. application Ser. No. 13/704,619, filed 16 Dec. 2012, which is a national phase of international patent application no. PCT/US2011/040781, filed 16 Jun. 2011, published as international publication no. WO 2011/159955 A1.

Various aspects of the present disclosure may be implemented in conjunction with OIS/OT-like signal processing algorithms for electrophysiology mapping. OIS/OT and related algorithms are discussed in more detail in U.S. provisional application No. 61/944,426, filed 25 Feb. 2014, U.S. application Ser. No. 15/118,522, filed 25 Feb. 2015, and international application no. PCT/US2014/011940, filed 16 Jan. 2014, which are hereby incorporated by referenced as though fully disclosed herein. Yet other embodiments of the present disclosure may be implemented in conjunction with various other electrophysiology mapping algorithms. For example, embodiments consistent with the present disclosure may utilize the electrode signal post-processing techniques, and electrophysiology mapping algorithms disclosed in the following publications, which are hereby incorporated by reference: Magtibay et al. JAHA 2017 (J Am Heart Assoc. 2017; 6: e006447. DOI: 10.1161/JAHA.117.006447) (see, e.g., pages 6 and 7, and section titled "Omnipoles Provide the Largest Possible Bipolar Voltages"); and Haldar et al. Circulation AE 2017 (Circ Arrhythm Electrophysiol. 2017; 10: e005018. DOI: 10.1161/CIRCEP.117.005018) (see, e.g., page 6, section titled "Omnipolar Voltage Amplitude Correlates to Largest Measurable Bipolar Vpp," and FIG. 4).

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various modules or other circuits may be implemented to carry out one or more of the operations and activities described herein and/or shown in the figures. In these contexts, a "module" is a circuit that carries out one or more of these or related operations/activities (e.g., controller circuitry that receives and processes signals from the electrodes indicative of electrophysiology characteristics of the tissue). For example, in certain of the above-discussed embodiments, one or more modules are discrete logic circuits or programmable logic circuits configured and arranged for implementing these operations/activities. In certain embodiments, such a programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules include a combination of a CPU hardware-based circuit and a set of instructions in the form of firmware, where the first module includes a first CPU hardware circuit with one set of instructions and the second module includes a second CPU hardware circuit with another set of instructions.

Certain embodiments are directed to a computer program product (e.g., nonvolatile memory device), which includes a machine or computer-readable medium having stored thereon instructions which may be executed by a computer (or other electronic device) to perform these operations/ activities.

The invention claimed is:

1. An electrophysiology catheter system comprising:
   a catheter shaft including an outer surface with a trench extending into the outer surface, wherein the trench comprises a helical portion and one or more laterally extending portions such that the trench extends helically and laterally about the catheter shaft;
   a flexible circuitry assembly coupled to the catheter shaft, the flexible circuitry assembly comprising:
      a helical portion extending longitudinally along and helically about a longitudinal axis of the catheter shaft and disposed within the helical portion of the trench, wherein the helical portion comprises a plurality of electrical traces sandwiched between one or more circuit board layers of the flexible circuitry; and
      one or more lateral portions extending from the helical portion and extending perpendicular to the longitudinal axis and disposed within the one or more laterally extending portions of the trench; and
      one or more electrodes configured and arranged on each of the one or more lateral portions to sense electrophysiological characteristics of tissue and receive electrical signals from the plurality of electrical traces,
      wherein the one or more lateral portions are weighted along the catheter shaft for enhanced electrophysiology mapping by the one or more electrodes disposed thereon; and
   heat shrink material applied over the flexible circuitry assembly, wherein the heat shrink material at least partially compresses the flexible circuitry assembly into the trench of the outer surface of the catheter shaft; and
   a distal tip coupled to a distal end of the catheter shaft.

2. The electrophysiology catheter system of claim 1, wherein the electrodes are spot electrodes, and a top surface of the spot electrodes are flush with the outer surface of the catheter shaft.

3. The electrophysiology catheter system of claim 2, the one or more spot electrodes are spaced along a length of the flexible circuitry assembly, and wherein the flexible circuitry assembly is configured and arranged, when coupled to the catheter shaft via the heat shrink material, to circumferentially and longitudinally distribute the spot electrodes about the catheter shaft.

4. The electrophysiology catheter system of claim 3, wherein the distal tip further includes a second flexible circuitry assembly, with a plurality of spot electrodes coupled thereto, radially offset from the flexible circuitry assembly.

5. The electrophysiology catheter system of claim 2, wherein the spot electrodes are further configured and arranged to facilitate electrophysiology mapping using orientation independent sensing/omnipolar technology.

6. The electrophysiology catheter system of claim 1, further including a biocompatible layer that extends over the catheter shaft, the distal tip, and the flexible circuitry assembly.

7. The electrophysiology catheter system of claim 1, wherein the flexible circuitry assembly extends distally and enters an internal lumen of the catheter shaft between a distal end of the catheter and the distal tip.

8. The electrophysiology catheter system of claim 1, further includes an ablation electrode on the distal tip, and the ablation electrode is communicatively coupled to the flexible circuitry assembly.

9. The electrophysiology catheter system of claim 8, wherein the flexible circuitry assembly is configured and arranged to facilitate sensing electrophysiology characteristics of the tissue in contact with the ablation electrode, and the distal tip further includes a lead wire that is communicatively coupled to the ablation electrode and is configured and arranged to facilitate high-current ablation energy delivery to the ablation electrode.

10. The electrophysiology catheter system of claim 1, wherein the flexible circuitry assembly includes a substrate comprised of polyimide, polyetheretherketone, polyester, polyethylene terephthalate material, or a combination thereof.

11. The electrophysiology catheter system of claim 1, wherein the flexible circuitry assembly includes a plurality of internal electrical traces extending along one or more substrate layers of the flexible circuitry assembly, the one or more electrodes are electrically coupled with at least one of the plurality of electrical traces through a solder pad.

12. The electrophysiology catheter system claim 1, wherein the one or more electrodes include a combination of electrophysiology mapping electrodes and impedance-based localization electrodes.

13. An electrophysiology catheter system comprising:
   a catheter comprising:
      a catheter shaft including an outer surface with a trench extending into the outer surface, wherein the trench comprises a helical portion and one or more laterally extending portions such that the trench extends helically and laterally about the catheter shaft;
      a distal tip coupled to the distal end of the catheter shaft;
      a catheter handle coupled to a proximal end of the catheter shaft; and
      a flexible circuitry assembly coupled to the catheter shaft, the flexible circuitry assembly comprising:
         a helical portion extending longitudinally along and helically about a longitudinal axis of the catheter shaft and disposed within the helical portion of the trench, wherein the helical portion comprises a plurality of electrical traces sandwiched between one or more circuit board layers of the flexible circuitry; and
         one or more lateral portions extending from the helical portion and extending perpendicular to the longitudinal axis and disposed within the one or more laterally extending portions of the trench; and
         one or more electrodes configured and arranged on each of the one or more lateral portions to sense electrophysiological characteristics of tissue and receive electrical signals from the plurality of electrical traces,

wherein the one or more lateral portions are weighted along the catheter shaft for enhanced electrophysiology mapping by the one or more electrodes disposed thereon; and heat shrink material applied over the flexible circuitry assembly, wherein the heat shrink material at least partially compresses the flexible circuitry assembly into the trench of the outer surface of the catheter shaft; and controller circuitry communicatively coupled to the one or more electrodes via the flexible circuitry assembly, the controller circuitry configured and arranged to receive signals from the one or more electrodes indicative of the electrophysiological characteristics of tissue in contact with the one or more electrodes.

14. The electrophysiology catheter system of claim 13, wherein the flexible circuitry assembly includes a plurality of internal electrical traces extending along one or more substrate layers, the traces communicatively coupling the one or more electrodes to the controller circuitry, and the one or more electrodes are ring electrodes surrounding at least a portion of the catheter shaft and are electrically coupled with at least one of the plurality of electrical traces on the flexible circuitry assembly; and the catheter further includes a biocompatible outer covering extending over at least a portion of the flexible circuitry assembly and the catheter shaft.

15. The electrophysiology catheter system of claim 13, further comprising at least one positioning electrode, wherein the at least one positioning electrode is configured to sense a signal indicative of both a position and orientation of a distal portion of the catheter by sensing an impedance, the at least one positioning electrode communicatively coupled to the flexible circuitry assembly; and the controller circuitry further configured and arranged to receive signals from the at least one positioning electrode indicative of the position and orientation of the distal portion of the catheter.

16. The electrophysiology catheter system of claim 13, further comprising at least one positioning electrode, wherein the at least one positioning electrode is configured to sense a signal indicative of both a position and orientation of a distal portion of the catheter by sensing a strength and orientation of a magnetic field in proximity to the positioning electrode, the at least one positioning electrode communicatively coupled to the flexible circuitry assembly; and the controller circuitry further configured and arranged to receive signals from the at least one positioning electrodes indicative of the position and orientation of the distal portion of the catheter.

17. The electrophysiology catheter system of claim 13, further comprising a plurality of positioning electrodes, wherein at least one of the plurality of positioning electrodes is configured to provide a signal indicative of both a position and orientation of a distal portion of the catheter by sensing an impedance and wherein at least one of the plurality of positioning electrodes is configured to provide a signal indicative of both a position and orientation of the distal portion of the catheter by sensing a strength and orientation of a magnetic field.

18. An electrophysiology catheter system comprising:

a catheter shaft with a trench extending into an outer surface of the catheter shaft, wherein the trench comprises a helical portion and one or more laterally extending portions such that the trench extends helically and laterally about the catheter shaft;

flexible circuitry assembly longitudinally and helically extending about, and coupled to, the catheter shaft, the flexible circuitry assembly including one or more spot electrodes configured and arranged to sense electrophysiological characteristics of tissue, the one or more spot electrodes disposed on one or more lateral portions of the flexible circuitry assembly such that the one or more spot electrodes are radially offset between longitudinally adjacent spot electrodes, wherein the one or more lateral portions extend perpendicular to a longitudinal axis of the catheter shaft and are disposed within the one or more laterally extending portions and extending a majority of a circumference of the catheter shaft, wherein the one or more lateral portions are weighted along the catheter shaft for enhanced electrophysiology mapping;

heat shrink material applied over the flexible circuitry assembly, wherein the heat shrink material at least partially compresses the flexible circuitry assembly into the outer surface of the catheter shaft; and a distal tip coupled to a distal end of the catheter shaft.

19. The electrophysiology catheter system of claim 18, wherein the flexible circuitry assembly is coupled to the catheter shaft via a reflow process.

20. The electrophysiology catheter system of claim 18, wherein the flexible circuitry assembly is coupled to the catheter shaft via an adhesive.

* * * * *